(12) United States Patent
Shehadeh

(10) Patent No.: US 10,344,284 B2
(45) Date of Patent: Jul. 9, 2019

(54) METHODS AND COMPOSITIONS EMPLOYING AN OSTEOPONTIN APTAMER TO DELIVER NUCLEIC ACIDS INTO SMOOTH MUSCLE, ENDOTHELIAL, CARDIAC AND PROGENITOR/STEM CELLS

(71) Applicant: Lina A. Shehadeh, Coconut Creek, FL (US)

(72) Inventor: Lina A. Shehadeh, Coconut Creek, FL (US)

( * ) Notice: Subject to any disclaimer, the term of this patent is extended or adjusted under 35 U.S.C. 154(b) by 0 days.

(21) Appl. No.: 15/036,357

(22) PCT Filed: Nov. 14, 2014

(86) PCT No.: PCT/US2014/065737
§ 371 (c)(1),
(2) Date: May 12, 2016

(87) PCT Pub. No.: WO2015/073848
PCT Pub. Date: May 21, 2015

(65) Prior Publication Data
US 2016/0272973 A1 Sep. 22, 2016

Related U.S. Application Data

(60) Provisional application No. 61/904,237, filed on Nov. 14, 2013.

(51) Int. Cl.
*A61K 48/00* (2006.01)
*C12N 15/11* (2006.01)
(Continued)

(52) U.S. Cl.
CPC .......... *C12N 15/115* (2013.01); *C12N 15/113* (2013.01); *C12N 15/1136* (2013.01);
(Continued)

(58) Field of Classification Search
CPC .......................... C12N 15/115; C12N 15/113; C12N 2310/16; A61K 48/00
(Continued)

(56) References Cited

FOREIGN PATENT DOCUMENTS

| WO | WO 09/102438 A2 | 8/2009 |
| WO | WO 13/142255 A2 | 9/2013 |

OTHER PUBLICATIONS

Stenvang et al. (Silence, 2012 vol. 3:pp. 1-17).*
(Continued)

*Primary Examiner* — Terra C Gibbs
(74) *Attorney, Agent, or Firm* — Alston & Bird LLP

(57) ABSTRACT

Various therapeutic polynucleotides are provided along with their use to treat a variety of disease states. The chimeric polynucleotides disclosed herein comprise an OPN aptamer linked to an OPN-specific therapeutic oligonucleotide in order to deliver the OPN-specific therapeutic polynucleotide to the site of OPN expression. Thus, the specificity of OPN aptamers allows delivery of therapeutic molecules to the site of unhealthy tissue. Accordingly, the chimeric polynucleotides disclosed herein can reduce at least one symptom of a disease or unhealthy condition by delivering an OPN-specific therapeutic oligonucleotide that interferes with a disease promoting factor.

22 Claims, 16 Drawing Sheets
(4 of 16 Drawing Sheet(s) Filed in Color)
Specification includes a Sequence Listing.

Structure of OPN Aptamer – premiR-30e Chimera (SEQ ID NO:12)

(51) Int. Cl.
*C07H 21/02* (2006.01)
*C07H 21/04* (2006.01)
*C12N 15/115* (2010.01)
*C12N 15/113* (2010.01)

(52) U.S. Cl.
CPC ........ *A61K 48/00* (2013.01); *C12N 2310/113* (2013.01); *C12N 2310/16* (2013.01); *C12N 2310/3519* (2013.01); *C12N 2320/30* (2013.01); *C12N 2320/32* (2013.01)

(58) Field of Classification Search
USPC .......................................... 514/44; 536/24.5
See application file for complete search history.

(56) References Cited

OTHER PUBLICATIONS

Zhou et al. (Nucleic Acids Research, 2009 vol. 37:3094-3109).*
Graf et al. (Circulation, 1999 vol. 96:3063-3071).*
Banerjee et al., "Aptamers: multifunctional molecules for biomedical research," Journal of Molecular Medicine, 91(12):1333-1342, (2013).
Lassalle et al., "Aptamers as Remarkable Diagnostic and Therapeutic Agents in Cancer Treatment," Current Drug Metabolism. 13(8):1130-1144, (2012).
Li et al., "Abstract 13586: Osteopontin RNA Aptamer Protects Against Pressure Overload-Induced Cardiac Dysfunction," Circulation, 128(Suppl 22):13586, (2013). [Retrieved from Biosciences Information Service, Database Biosis, Database Accession No. PREV201400366016].
Mi et al., "RNA Aptamer Blockade of Osteopontin Inhibits Growth and Metastasis of MDA-MB231 Breast Cancer Cells," Molecular Therapy, 17(1):153-61, (2009). [Published online on Nov. 4, 2008].
Que-Gewirth et al., "Gene therapy progress and prospects: RNA aptamers," Gene Therapy, 14(4):283-291, (2007).
Talbot et al., "Pharmacokinetic characterization of an RNA aptamer against osteopontin and demonstration of in vivo efficacy in reversing growth of human breast cancer cells," Surgery, 150(2):224-230, (2011).
WIPO Application No. PCT/US2014/065737, International Preliminary Report on Patentability, completed Feb. 2, 2016.
WIPO Application No. PCT/US2014/065737, International Search Report, dated Mar. 16, 2015.
WIPO Application No. PCT/US2014/065737, Written Opinion of the International Searching Authority, dated Mar. 16, 2015.
Zhou et al., "Functional In Vivo Delivery of Multiplexed Anti-HIV-1 siRNAs via a Chemically Synthesized Aptamer With a Sticky Bridge," Molecular Therapy, 21(1):192-200, (2013). [Published online on Nov. 20, 2012].

* cited by examiner

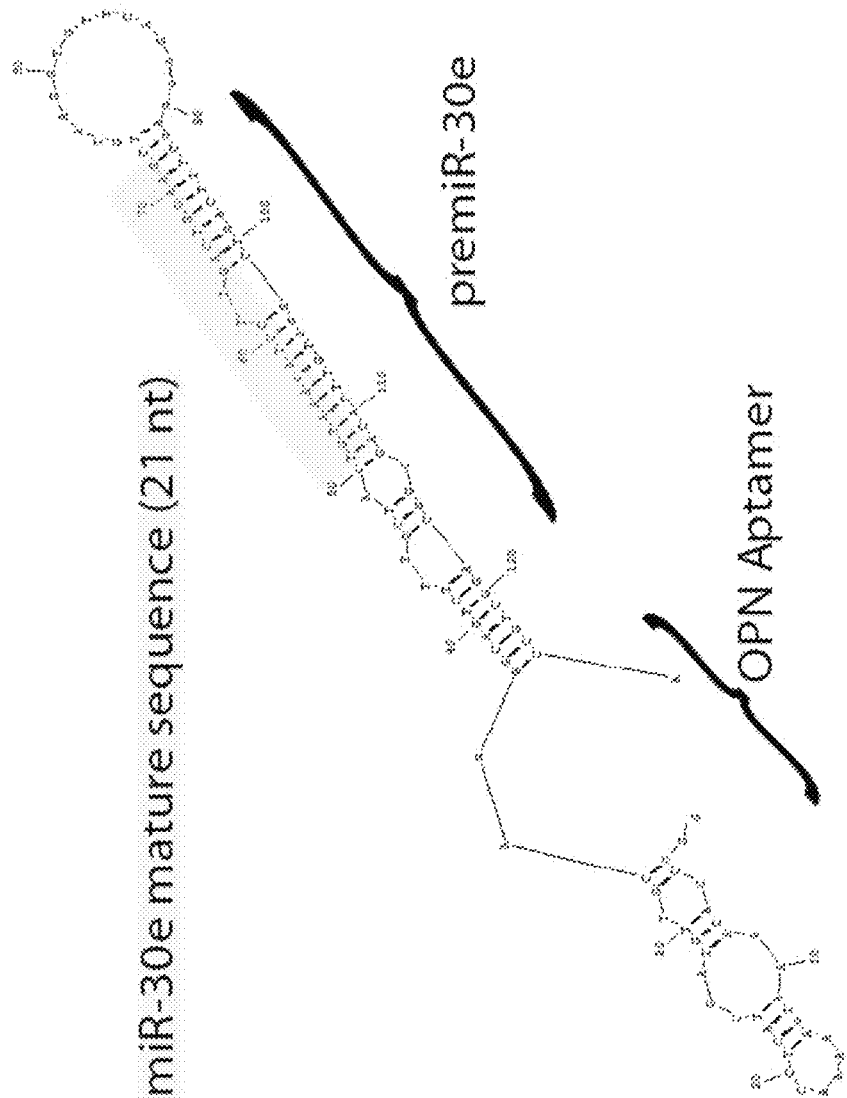
Figure 1. Structure of OPN Aptamer – premiR-30e Chimera (SEQ ID NO:12)

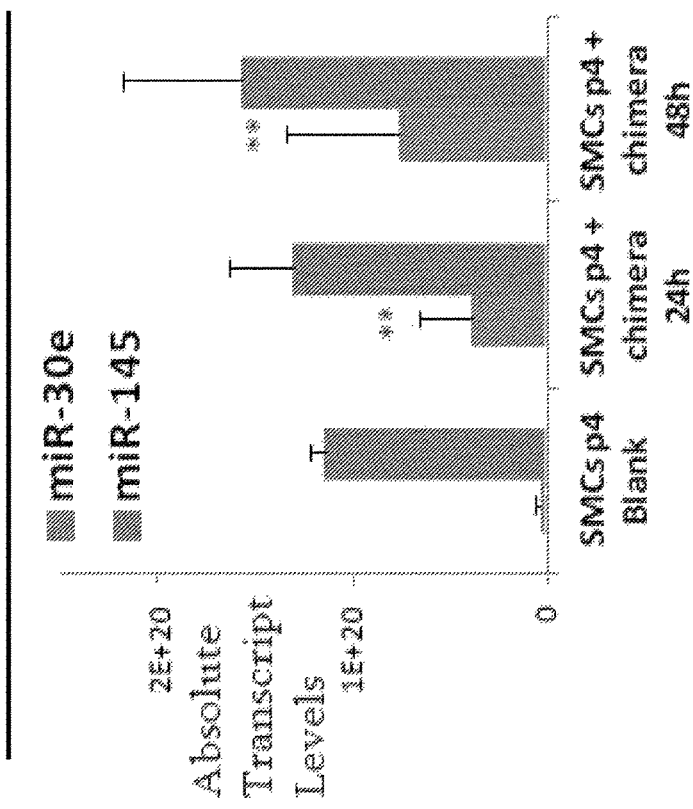
Figure 2. OPN Aptamer – miR-30e Chimera Treatment Delivers miR-30e into Mouse Aortic Smooth Muscle Cells.

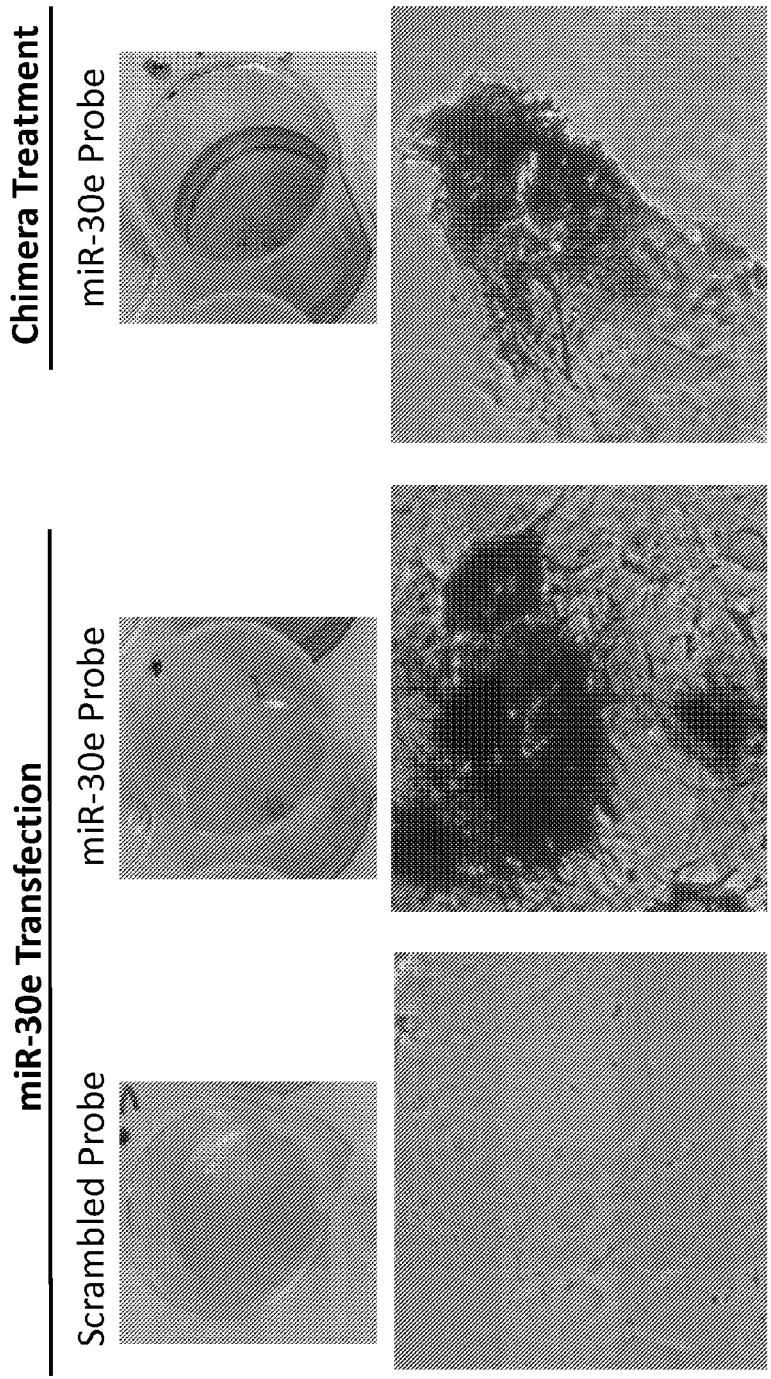
Figure 3. OPN Aptamer – miR-30e Chimera Treatment Delivers miR-30e into Mouse Bone Marrow-Derived Mesenchymal Stem Cells.

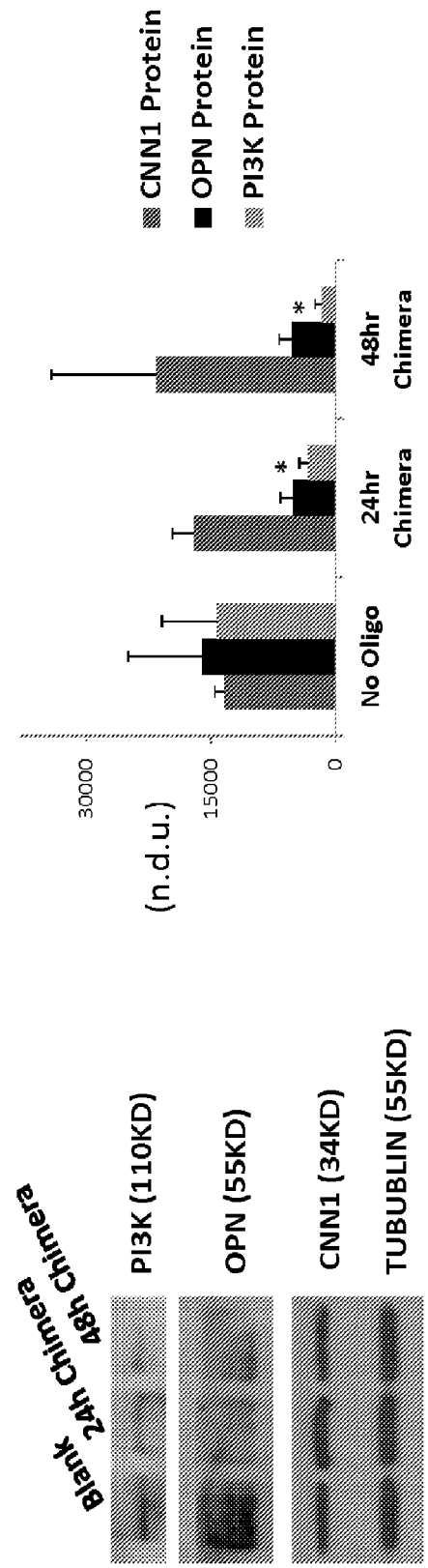
Figure 4. OPN Aptamer – miR-30e Chimera Treatment is Functional in Mouse Aortic Smooth Muscle Cells.

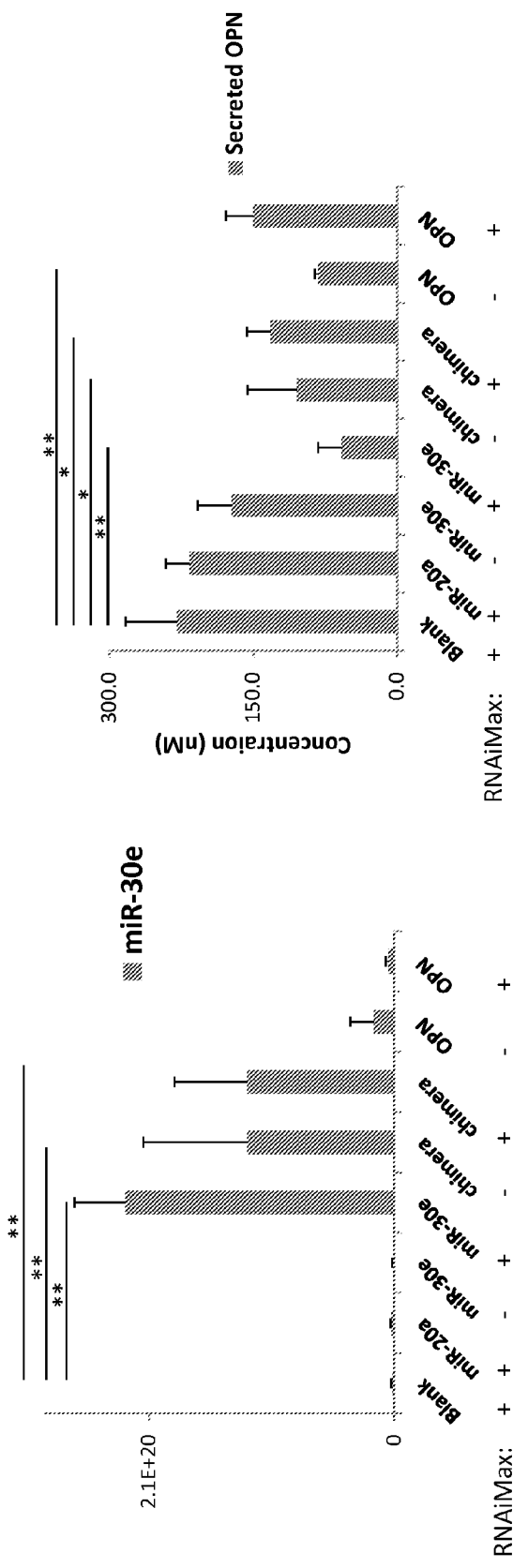
Figure 5. OPN Aptamer – miR-30e Chimera Treatment is Functional in Mouse Aortic Smooth Muscle Cells.

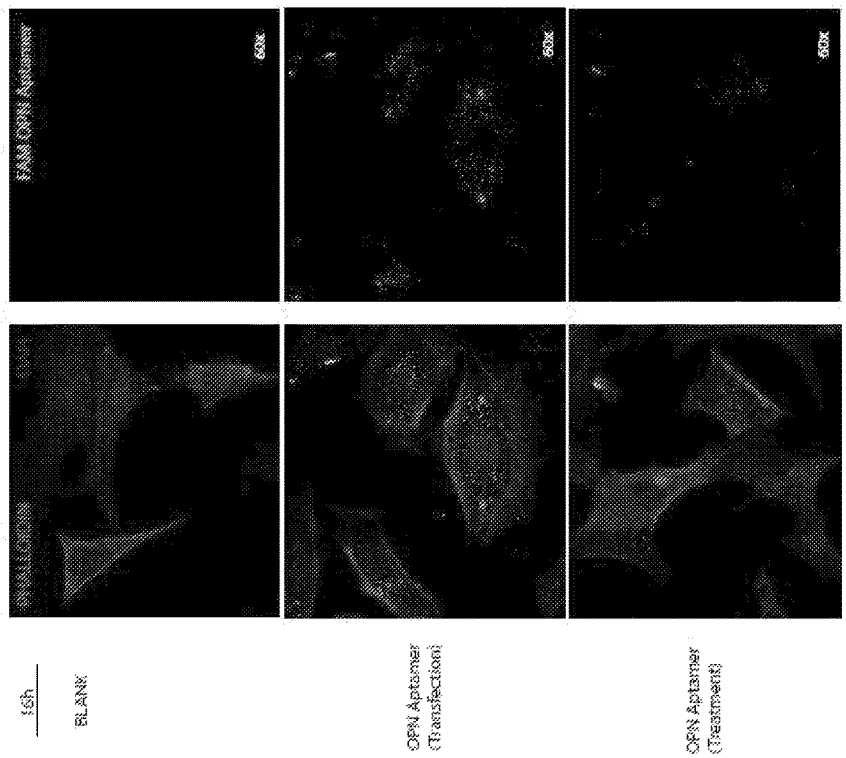
Figure 6. FAM-OPN Aptamer Treatment Delivers Aptamer into Mouse Embryonic Fibroblasts.

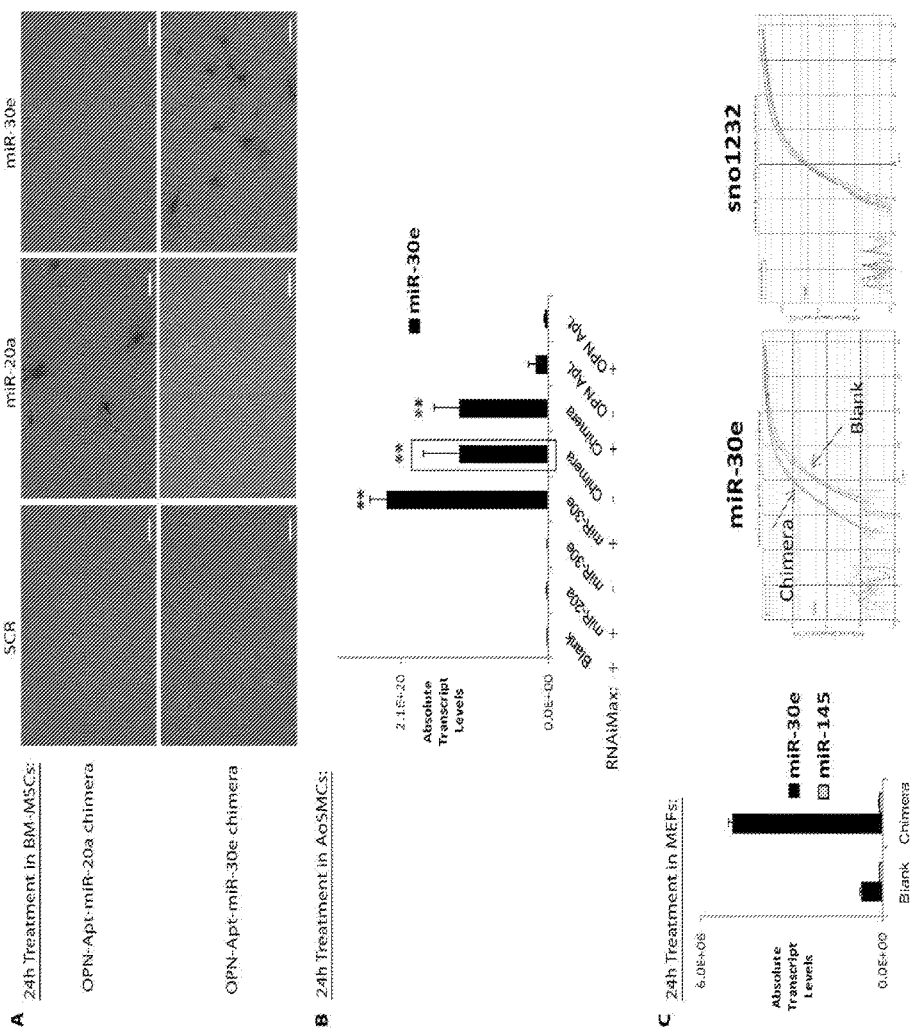
Figure 7. OPN Aptamer-miR-30e or –miR-20a Chimera Treatments in Mesenchymal Stem Cells, Smooth Muscle Cells, or Mouse Embryonic Fibroblasts

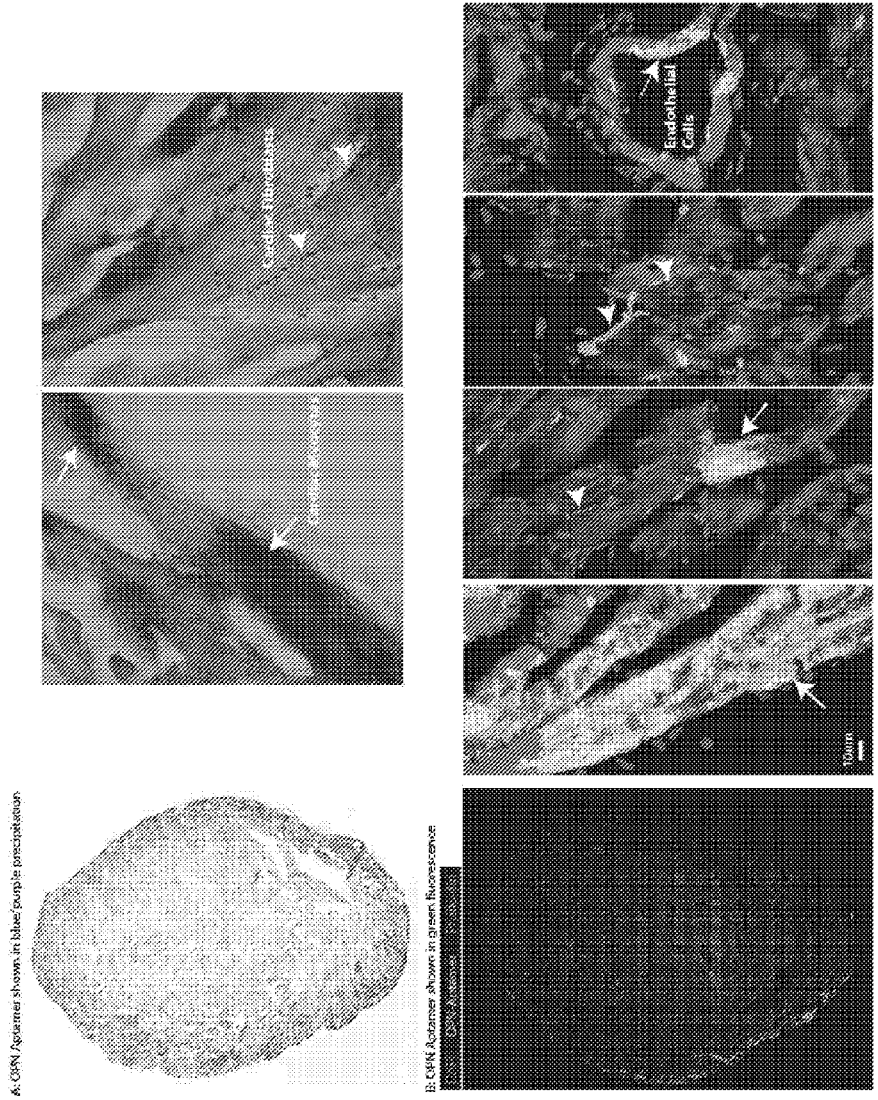
Figure 8. DIG-OPN Aptamer Treatment Delivers Aptamer into Banded Mouse Heart

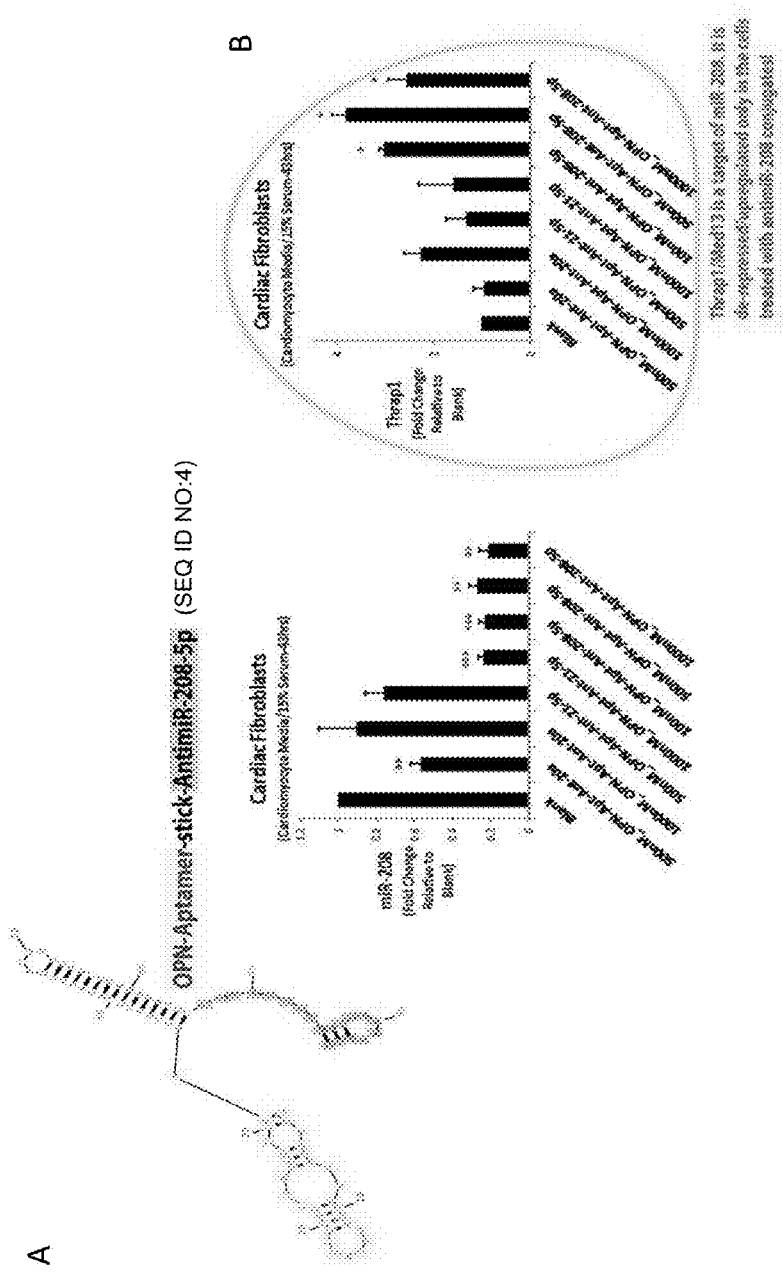
Figure 9. OPN Aptamer-antimiR-208 Chimera Delivers Functional antimiR-208 to Mouse Cardiac Fibroblasts

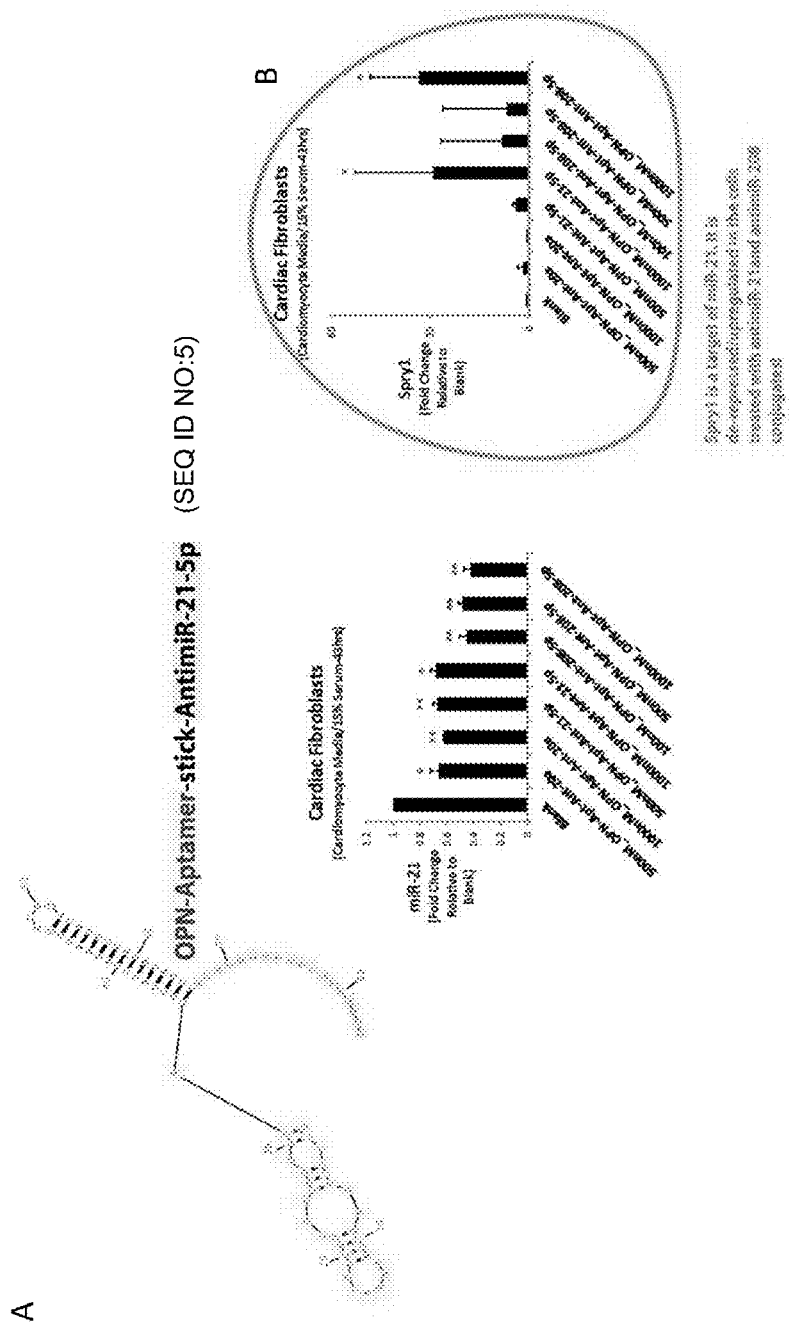
Figure 10. OPN Aptamer-antimiR-21 Chimera Delivers Functional antimiR-21 to Mouse Cardiac Fibroblasts

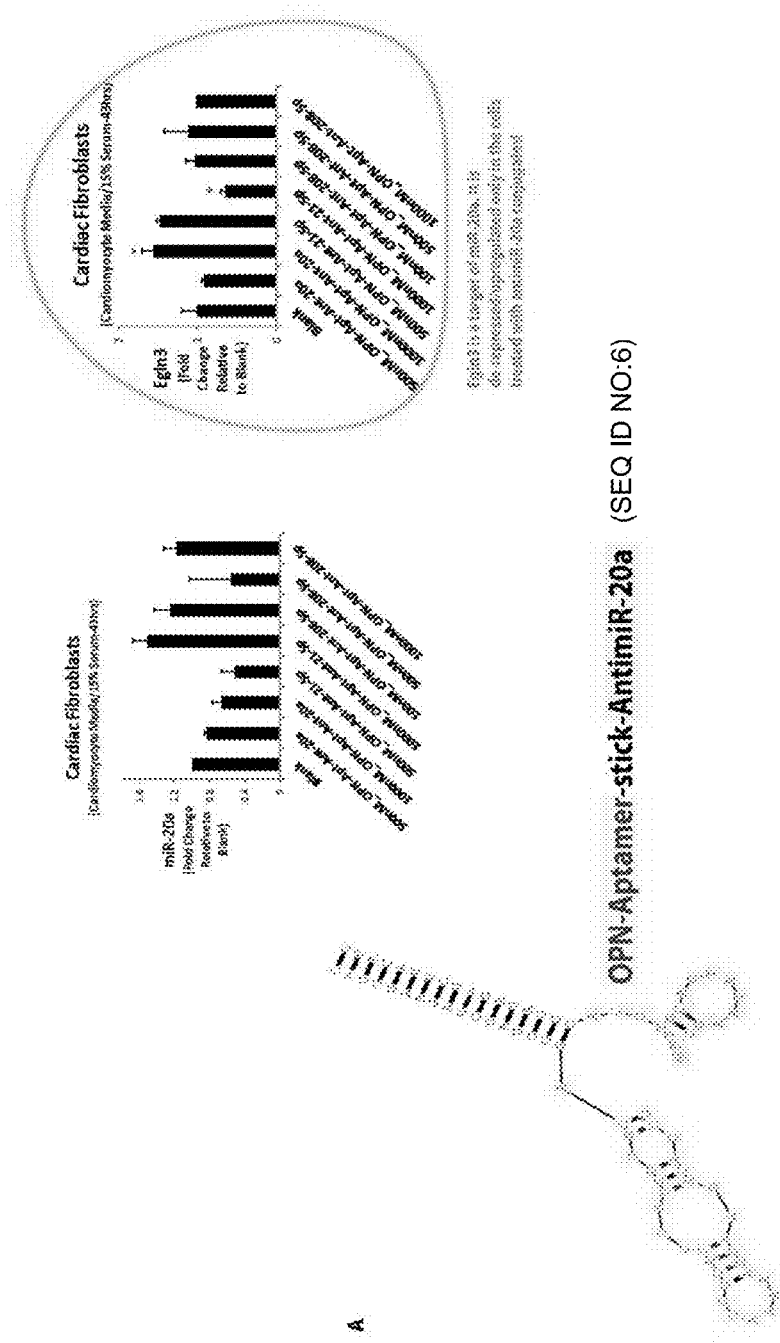
Figure 11. OPN Aptamer-antimiR-20a Chimera Delivers Functional antimiR-20a to Mouse Cardiac Fibroblasts

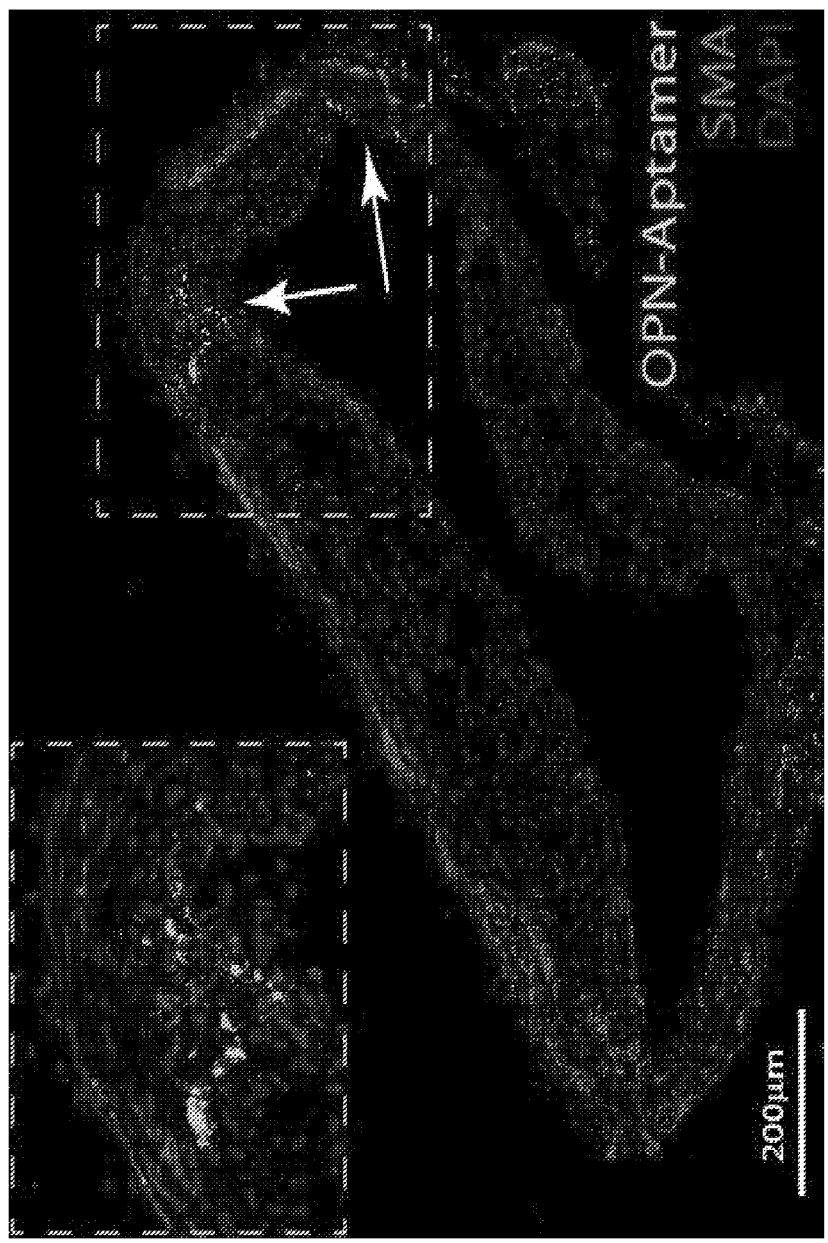
Figure 12. DIG-OPN Aptamer Treatment Delivers Aptamer into Atherogenic Plaque

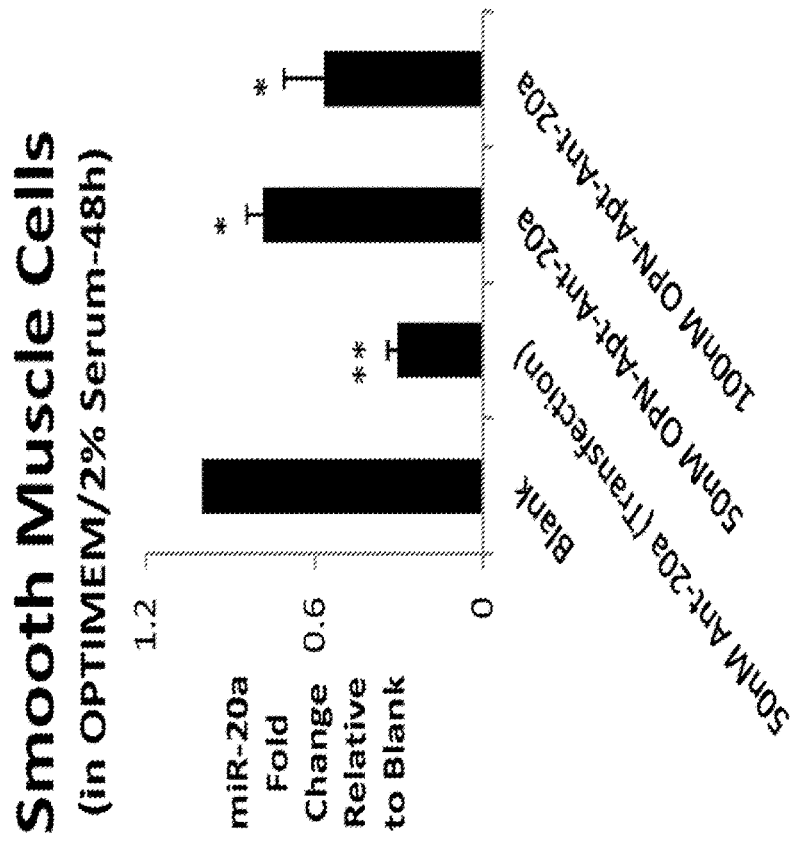
Figure 13. OPN Aptamer-antimiR-20a Chimera Delivers Functional antimiR-20a to Mouse Smooth Muscle Cells

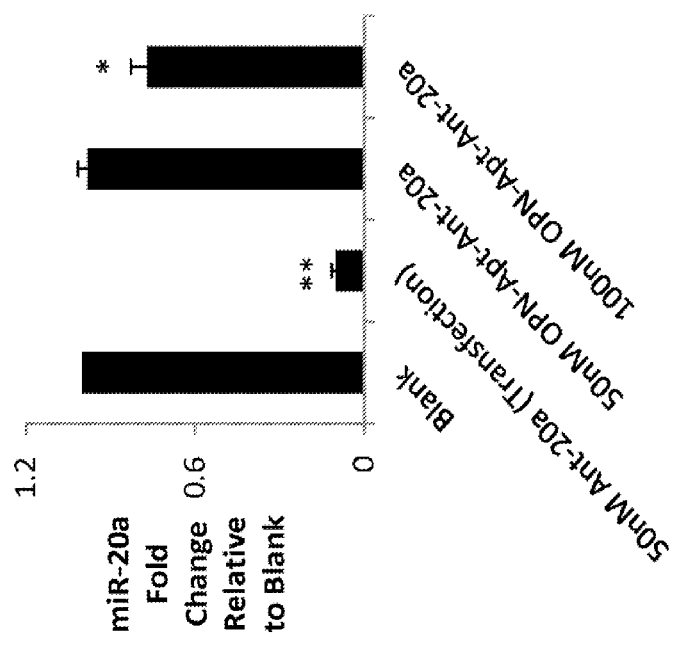
Figure 14. OPN Aptamer-antimiR-20a Chimera Delivers Functional antimiR-20a to Mouse Smooth Muscle Cells in Osteogenic Media

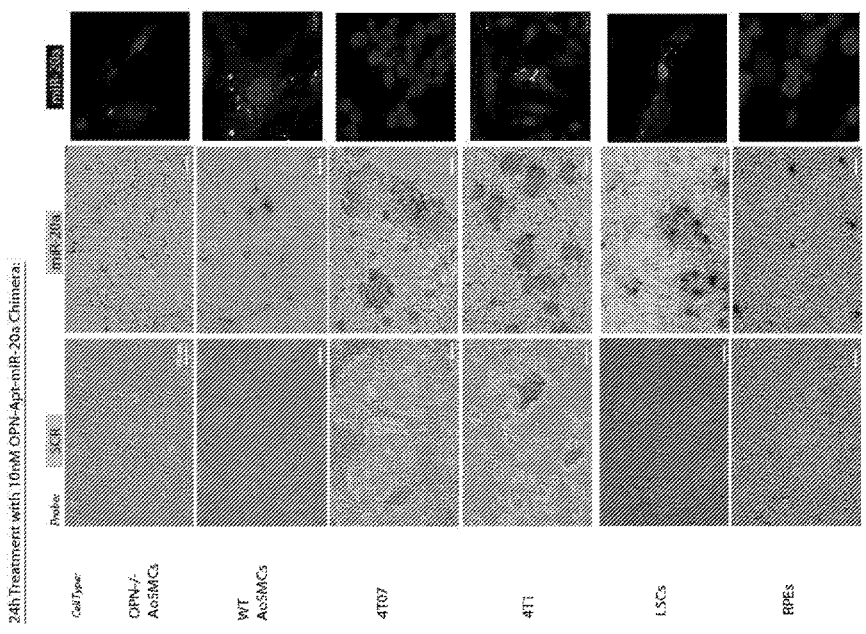
Figure 15. OPN aptamer-miR-20a Chimera Treatment Delivers miR-20a Only to OPN-Expressing Cells

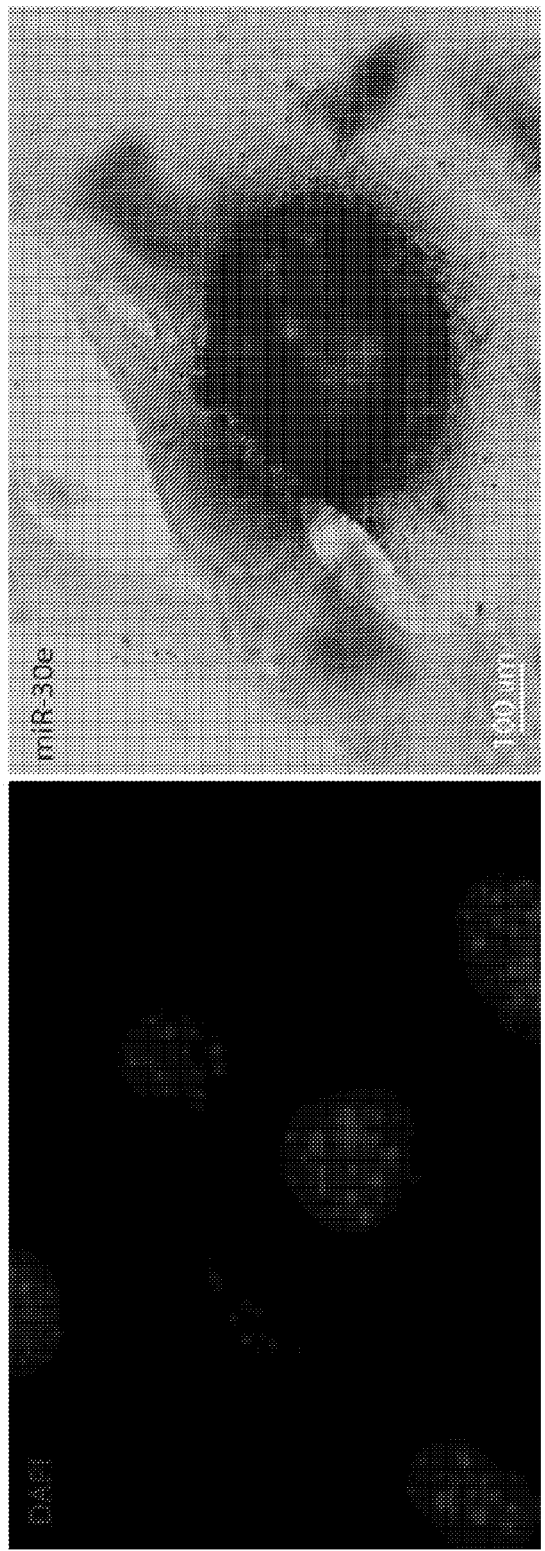
Figure 16. OPN Aptamer miR-30e Chimera Treatment Delivers miR-30e to Mesenchymal Stem Cells

METHODS AND COMPOSITIONS EMPLOYING AN OSTEOPONTIN APTAMER TO DELIVER NUCLEIC ACIDS INTO SMOOTH MUSCLE, ENDOTHELIAL, CARDIAC AND PROGENITOR/STEM CELLS

CROSS REFERENCE TO RELATED APPLICATIONS

This application is a US national stage of PCT/US2014/065737 filed Nov. 14, 2014, which claims the benefit of U.S. Provisional Application No. 61/904,237 filed Nov. 14, 2013, all of which are incorporated herein by reference.

FEDERALLY SPONSORED RESEARCH OR DEVELOPMENT

The invention was made with United States Government support under grant no. K01 AG040468 from the National Institute of Health. The United States Government has certain rights in this invention.

REFERENCE TO A SEQUENCE LISTING

This application includes an electronic sequence listing in a file named 479356SEQLST.txt, created on Dec. 26, 2017 and containing 4,884 bytes, which is hereby incorporated by reference in its entirety for all purposes.

FIELD OF THE INVENTION

This invention relates to therapeutic oligonucleotides.

REFERENCE TO ELECTRONICALLY-SUBMITTED SEQUENCE LISTING

The official copy of the sequence listing is submitted electronically via EFS-Web as an ASCII formatted sequence listing with a file named 454837SEQLIST.txt, created on Nov. 14, 2014, and having a size of 4 KB and is filed concurrently with the specification. The sequence listing contained in this ASCII formatted document is part of the specification and is herein incorporated by reference in its entirety.

BACKGROUND OF THE INVENTION

Oligonucleotides can modulate a vast variety of cellular functions and therefore represent a promising alternative to conventional therapies. Among the different oligonucleotides with therapeutic potential are aptamers, transcription factor-binding decoy oligonucleotides, ribozymes, triplex-forming oligonucleotides, immunostimulatory CpG motifs, antisense oligonucleotides, small interfering RNAs (siRNAs), long non coding RNAs (lncRNAs), mRNAs, microRNAs, and antimiRs. Their two main advantages over protein- or peptide-based strategies are the high specificity for their target and being non-immunogenic. However, despite these advances, a major bottleneck to the development of nucleic acid-based strategies for treatment and prevention of human diseases is the inefficient means to effectively deliver these oligonucleotides into the desired target cells. Although viral vectors have been widely used to transfer nucleic acids into cells, they bear an inherent risk for the patient to encounter severe immunological responses or even develop cancer. As a result of these problems there has been an urgent need in recent years to the development of non-viral delivery systems. Currently, liposomes and cationic polymers are used as a standard tool to transfect cells in vitro. However, these procedures lack significant efficiency in primary cells and are highly toxic rendering them mostly unfeasible for in vivo applications.

BRIEF SUMMARY OF THE INVENTION

A chimeric polynucleotide is provided herein comprising an OPN aptamer linked to an OPN-specific therapeutic oligonucleotide. The chimeric polynucleotide can comprises a polynucleotide comprising SEQ ID NO: 1 or an active variant or fragment thereof having at least 80%, 90%, 92%, 95%, 96%, 97%, 98%, or 99% sequence identity to SEQ ID NO: 1. The OPN-specific therapeutic oligonucleotide can comprise a microRNA, antiMicro RNA oligonucleotide (antimiR), double stranded RNA interference oligonucleotide, double stranded RNA with microRNA activity, antisense oligonucleotide, pre-miRNA, another aptamer or a mRNA coding for microRNAs, or shRNAs. For example, the OPN-specific therapeutic oigonuclotide can comprise an antimiR specific for a miRNA, wherein the mRNA target of the miRNA is Thrap1, Med13, Spry1, and/or Egln3. The mRNA target can be a) Thrap1 or Med13 and the miRNA comprises miR-208-5p; b) Spry1 and the miRNA comprises miR-21-5p; or c) Egln3 and the miRNA comprises miR-20a. Accordingly, the miRNA can comprise a) miR-208-5p and the antimiR comprises the nucleotide sequence set forth in SEQ ID NO: 7 or active fragments or variants thereof having at least 80%, 90%, 92%, 95%, 96%, 97%, 98%, or 99% sequence identity to SEQ ID NO: 7; b) miR-21-5p and the antimiR comprises the nucleotide sequence set forth in SEQ ID NO: 8 or active fragments or variants thereof having at least 80%, 90%, 92%, 95%, 96%, 97%, 98%, or 99% sequence identity to SEQ ID NO: 8; or c) miR-20a and the antimiR comprises the nucleotide sequence set forth in SEQ ID NO: 9 or active fragments or variants thereof having at least 80%, 90%, 92%, 95%, 96%, 97%, 98%, or 99% sequence identity to SEQ ID NO: 9.

Alternatively, the miRNA can comprise miR-30e wherein miR-30e comprises the nucleotide sequence set forth in SEQ ID NO: 2 or active fragments or variants thereof having at least 80%, 90%, 92%, 95%, 96%, 97%, 98%, or 99% sequence identity to SEQ ID NO: 2. The chimeric polynucleotide can comprise a nucleotide sequence selected from the group consisting of SEQ ID NOs: 3, 4, 5, and 6, or an active variant or fragment thereof having at least 80%, 90%, 92%, 95%, 96%, 97%, 98%, or 99% sequence identity to SEQ ID NO: 3, 4, 5, or 6. The OPN aptamer can be directly linked to the OPN-specific therapeutic oligonucleotide or can comprise a linker, such as a sticky bridge linker.

Further provided are methods for delivering an OPN-specific therapeutic oligonucleotide to unhealthy tissue comprising administering a chimeric polynucleotide comprising an OPN aptamer linked to the OPN-specific therapeutic oligonucleotide. In such methods, the OPN aptamer can comprise a polynucleotide comprising SEQ ID NO: 1 or an active variant or fragment thereof. Further, the OPN-specific therapeutic oligonucleotide can comprise a microRNA (miRNA), antiMicro RNA (antimiR), double stranded RNA interference oligonucleotide, double stranded RNA with microRNA activity, antisense oligonucleotide, pre-miRNA, other aptamers, or a mRNA coding for microRNAs, or shRNAs. Wherein the OPN-specific therapeutic oligonucleotide comprises an antimiR, the level of the miRNA corresponding to the antimiR can be decreased, and wherein the level of the mRNA target of the miRNA can be increased following delivery of the OPN-specific therapeutic oligonucleotide. The mRNA target can be Thrap1/Med13, Spry1, and/or Egln3 such that wherein the mRNA target is: a) Thrap1 or Med13 and the miRNA comprises miR-208-5p; b) Spry1 and the miRNA comprises miR-21-5p; or c) Egln3 and the miRNA comprises miR-20a. Wherein the miRNA comprises: a) miR-208-5p and the antimiR can comprise the nucleotide sequence set forth in SEQ ID NO: 7 or active fragments or variants thereof having at least 80%, 90%, 92%, 95%, 96%, 97%, 98%, or 99% sequence identity to SEQ ID NO: 7; b) miR-21-5p and the antimiR can comprise the nucleotide sequence set forth in SEQ ID NO: 8 or active fragments or variants thereof having at least 80%, 90%, 92%, 95%, 96%, 97%, 98%, or 99% sequence identity to SEQ ID NO: 8; or c) miR-20a and the antimiR can comprise the nucleotide sequence set forth in SEQ ID NO: 9 or active fragments or variants thereof having at least 80%, 90%, 92%, 95%, 96%, 97%, 98%, or 99% sequence identity to SEQ ID NO: 9.

In certain methods, the miRNA could also comprise miR-30e, such as the nucleotide sequence set forth in SEQ ID NO: 2 or active fragments or variants thereof having at least 80%, 90%, 92%, 95%, 96%, 97%, 98%, or 99% sequence identity to SEQ ID NO: 2. In some methods, the OPN aptamer is directly linked to the OPN-specific therapeutic oligonucleotide or can be linked to the OPN-specific therapeutic oligonucleotide with a linker, such as a sticky bridge linker. The method can deliver a chimeric polynucleotide comprising a nucleotide sequence selected from the group consisting of SEQ ID NO: 3, 4, 5, and 6, or an active variant or fragment thereof having at least 80%, 90%, 92%, 95%, 96%, 97%, 98%, or 99% sequence identity to SEQ ID NO: 3, 4, 5, or 6.

In some embodiments, a therapeutically effective amount of the OPN-specific therapeutic oligonucleotide is delivered to the unhealthy tissue. The OPN-specific therapeutic oligonucleotide can be internalized into cells of the unhealthy tissue. In certain embodiments, the unhealthy tissue expresses OPN. The method can deliver the OPN-specific therapeutic oligonucleotide to the unhealthy tissue, such as inflamed tissue, and the inflammation can be reduced following delivery of the OPN-specific therapeutic oligonucleotide to the unhealthy tissue. The unhealthy tissue can also be cardiac tissue wherein the OPN-specific therapeutic oligonucleotide is internalized by cardiac muscle cells, cardiac fibroblasts, and/or thoracic plaque. The OPN-specific therapeutic oligonucleotide can be delivered to cells of unhealthy tissue in vitro or in a subject. The subject can have an unhealthy condition selected from the group consisting of: inflammation, Crohn's disease, cancer, atherosclerosis, aortic abdominal aneurysms, autoimmune diseases, lupus, multiple sclerosis, rheumatoid arthritis, cardiovascular disease, heart failure, and Parkinson's disease. In some methods, at least one symptom of the unhealthy condition is reduced. The subject can comprise an OPN receptor wherein the OPN-specific therapeutic oligonucleotide does not bind said OPN receptor.

In some embodiments, the chimeric polynucleotide is formulated as a pharmaceutical composition. Further, in some methods, no transfection reagent is administered for delivery of the OPN-specific therapeutic oligonucleotide.

BRIEF DESCRIPTION OF THE DRAWINGS

The patent application file contains at least one drawing executed in color. Copies of this patent application with color drawing(s) will be provided by the Office upon request and payment of the necessary fee.

FIG. 1 shows the secondary structure of OPN-Aptamer-miR-30e Chimera (SEQ ID NO: 12). OPN aptamer was transcribed with premiR-30e without the use of any linkers. Region highlighted in yellow corresponds to miR-30e mature sequence.

FIG. 2 shows the OPN aptamer delivers miR-30e into Smooth Muscle Cells (SMCs). SMCSp4 were treated with OPN-premiR-30e chimera. MiR-30e transcript levels were highly induced in the chimera-treated SMCs as measured by qPCR. MiR-145 was used as a negative control and was not significantly changed. N=3 per group. **=p<0.01.

FIG. 3 shows the In Situ Hybridization (ISH) confirms delivery of miR-30e into chimera treated Mesenchymal Stem Cells (MSCs). MSCs were transfected with 100 nM miR-30e oligos, or treated with 100 nM OPN-Aptamer-miR-30e chimera, for 24 hrs. ISH signal is strong (purple) with the miR-30e ISH probe in transected positive control cells and in the chimera-treated cells. The Scrambled (SCR) ISH probe shows no signal.

FIG. 4 shows the OPN-Aptamer-miR-30e chimera is functional in SMCs. SMCsp4 were treated with OPN-AptmiR-30e chimera for 24 or 48 hrs, and western show that miR-30e and/or OPN aptamer is functional by regulating Cnn1, OPN, and PI3K intracellular proteins. N=3 per group. *=p<0.05.

FIG. 5 shows the OPN-Apt-miR-30e chimera is functional in SMCs. SMCSp9 were treated or transfected with 2'F oligos synthesized in the lab. Top panel shows qPCR quantification of mature sequence of miR-30e. MiR-30e was significantly over-expressed when cells were transfected with premiR-30e (Fold Change=120.20; p=0.00004), transfected with OPN-premiR-30e chimera (Fold Change: 59.68 p=0.0006), or treated with OPN-premiR-30e chimera (Fold Change=71.51, p=0.001). Bottom panel shows levels of secreted Osteopontin (OPN) protein as measured by ELISA. N=3 per group.

FIG. 6 shows the FAM-labeled OPN aptamer delivers into Mouse Embryonic Fibroblasts (MEFs). Confocal microscopy confirms internalization of FAM-labeled OPN aptamer into MEFs 16 hours post treatment.

FIG. 7 shows that OPN-aptamer chimeras deliver miR-30e or miR-20a to mouse aortic SMCs and mouse bone marrow derived mesenchymal stem cells (MSCs).

FIG. 8 shows successful delivery of OPN Aptamer to the failing heart.

FIG. 9 shows delivery of antimiR-208-5p to cardiac fibroblast cells (in cardiac media) and subsequent decrease in the level of miR-208. The figure demonstrates that OPN can deliver antimiR-208-5p to cardiac fibroblast cells, effectively decreasing the level of miR-208 present in the cells and effectively de-repressing Thrap1, the target of miR-208.

FIG. 10 shows delivery of antimiR-21-5p to cardiac fibroblast cells (in cardiac media) and subsequent decrease in the level of miR-21. The figure demonstrates that OPN can deliver antimiR-21-5p to cardiac fibroblast cells, effectively decreasing the level of miR-21 present in the cells and effectively de-repressing Spry1, the target of miR-21.

FIG. 11 shows delivery of antimiR-20a to cardiac fibroblast cells (in cardiac media) and subsequent decrease in the level of miR-20a. The figure demonstrates that OPN can deliver antimiR-20a to cardiac fibroblast cells, effectively decreasing the level of miR-20a present in the cells and effectively de-repressing the Egln3, the target of miR-20a.

FIG. 12 shows that OPN aptamer homes to plaque in atherogenic APOE−/− mouse.

FIG. 13 shows delivery of antimiR-20a to smooth muscle cells in OPTIMEM/2% Serum using transfection (positive control) or OPN aptamer delivery. The figure demonstrates that OPN can deliver antimiR-20a to smooth muscle cells and effectively decrease the level of miR-20a present in the cells.

FIG. 14 shows delivery of antimiR-20a to smooth muscle cells in Osteogenic Media/10% Serum using transfection (positive control) or OPN aptamer delivery. The figure demonstrates that OPN can deliver antimiR-20a to smooth muscle cells and effectively decrease the level of miR-20a present in the cells.

FIG. 15 shows that the conjugate/chimera of OPN-aptamer-miR-20a delivers miR-20a to: 1) Mouse WT SMCs (that express OPN) but not OPN−/− SMCs; 2) 4T1 breast cancer cells that express OPN, but not 4T07 breast cancer cells that lack OPN; and 3) Human Corneal Limbal Stem Cells (LSCs) and Retinal Pigment Epithelial cells (RPEs).

FIG. 16 shows OPN-aptamer-miR-30e chimera delivers miR-30e to mouse bone marrow derived MSCs.

DETAILED DESCRIPTION OF THE INVENTION

I. Overview

The present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

To date, most approaches for targeted oligonucleotide delivery have aimed for specific cell surface receptors (e.g. cell surface receptor agonist or antagonist). In this study, we sought to target a ligand rather than a cell receptor for oligonucleotide delivery. Our ligand of interest is osteopontin (OPN). Osteopontin is a glycoprotein that is upregulated in numerous diseases including cancer, heart failure, and fibrotic tissue. In diseased or inflamed tissue, cells overexpress the receptors for osteopontin such as various integrin and CD44/hyaluronic acid receptors. A major advantage for targeting osteopontin is that OPN has chemotactic properties which serve as a guide to the diseased tissue (analogous to mesenchymal stem cells that home to the diseases tissue). Therefore, we used an OPN aptamer RNA sequence that was reported to 1) block OPN pathways in the extracellular space of breast cancer cells, and 2) not internalized by cells without transfection reagents. We conjugated the OPN aptamer sequence to oligonucleotides (e.g. premiR-30e, antimiR-208-5p, antimiR-21-5p, antimiR-20a) and treated various cell types with the OPN-aptamer-RNA chimera without any transfection reagents. We found that the interfering RNA oligos were delivered into the chimera-treated cells supporting our hypothesis that the OPN molecules carried the oligonucleotide via the OPN aptamer into the cells. This technology can serve as a platform for delivering therapeutic oligonucleotides into inflamed tissue.

II. Chimeric Polynucleotides

The chimeric polynucleotides disclosed herein comprise an OPN aptamer linked to an OPN-specific therapeutic oligonucleotide in order to deliver the OPN-specific therapeutic polynucleotide to the site of OPN expression. Thus, the specificity of OPN aptamers allows delivery of therapeutic molecules to the site of unhealthy tissue. The term "chimeric" "conjugate" or "conjugated" refers to a polynucleotide comprising an OPN aptamer linked to an OPN-specific therapeutic oligonucleotide or another aptamer. In some embodiments the OPN aptamer can be a RNA aptamer and the OPN-specific therapeutic oligonucleotide is comprised of a DNA sequence. In other embodiments, the chimeric or conjugate molecule comprises an RNA OPN aptamer linked to another RNA aptamer.

The ability of nucleic acids, and single-stranded nucleic acids in particular, to fold into specific and stable secondary structures has led to identification of nucleic acid sequences (i.e., aptamers) with structures that can bind preferentially to selected targets and also discriminate between subtle molecular differences within the target. Unless otherwise apparent from context, the term "aptamer" refers to a nucleic acid molecule that naturally folds into specific and stable secondary structures that enable it to bind to a selected target. The term "nucleic acid", "polynucleotide" or "oligonucleotide" refers to single-stranded or double-stranded deoxyribonucleic acid (DNA) or ribonucleic acid (RNA) and any chemical modifications thereof. Such modifications can include, for example, modifications at cytosine exocyclic amines, substitution of 5-bromo-uracil, backbone modifications, methylations, unusual base-pairing combinations, and the like. In some cases, aptamers are isolated nucleic acids.

The term "isolated," when referring to an aptamer or a nucleic acid, means that the aptamer or nucleic acid is a predominant aptamer or nucleic acid species in a composition. An aptamer or nucleic acid can be considered to be a predominant aptamer or nucleic acid species in a composition if it represents at least about 5%, at least about 10%, at least about 20%, at least about 30%, at least about 40%, at least about 50%, at least about 60%, at least about 70%, at least about 80%, at least about 90%, at least about 95%, or 100% of the aptamers or nucleic acid species in the composition. This can be determined, for example, using analytical chemistry techniques such as polyacrylamide gel electrophoresis, high performance liquid chromatography, and the like.

The term "OPN aptamer" refers to any aptamer that preferentially binds to osteopontin (OPN). The term "preferential binding" or "preferentially binds" means that an aptamer or other molecule binds with greater affinity, with greater avidity, more readily, and/or with greater duration to a target than it binds to at least one unrelated non-target. An aptamer or other molecule that preferentially binds to a first target could preferentially bind to a second target. Thus, preferential binding does not require, but can include, exclusive binding. Many assays can be used to qualitatively or quantitatively detect or measure binding of OPN aptamers to OPN. For example, an Enzyme-Linked Aptamer Sorbent Assay (ELASA) can be used. Assays involving amplification of the bound aptamer (e.g., qPCR) or RNA from the aptamer-bound OPN (e.g., qRT-PCR) can be used. Flow cytometry methods as described in U.S. Pat. No. 5,853,984 can be used. Microarrays, BIAcore assays, differential centrifugation, chromatography, electrophoresis, immunoprecipitation, optical biosensors, and other surface plasmon resonance assays can be used as described in WO 2011/061351. Other assays that can be used are calorimetric analysis and dot blot assays. Moreover, just as the enzyme-linked immunosorbent assay (ELISA) was adapted for aptamers in the ELASA assay, any other assays involving OPN-binding antibodies can be adapted for use with the OPN aptamers disclosed herein in place of the antibodies. Such assays include immunometric assays such as radioimmunoassays, flow cytometry assays, blotting applications, anisotropy, membrane assays, biosensors, and the like. Any other assays known in the art can also be used or adapted to detect or measure binding of OPN aptamers to OPN. The OPN aptamer described herein can comprise the nucleotide sequence GCCACAGAAUGAAAAACCUCAUCGAUGUUGCA (SEQ ID NO:1) or an active variant or fragment thereof.

The length of the OPN aptamers of the invention is not limited, but typical aptamers have a length of about 10 to about 100 nucleotides, e.g., about 20 to about 80 nucleotides, about 30 to about 50 nucleotides, or about 40 nucleotides. In certain embodiments, the aptamer may have additional nucleotides attached to the 5'- and/or 3' end. The additional nucleotides may be, e.g., part of primer sequences, restriction endonuclease sequences, or vector sequences useful for producing the aptamer.

The polynucleotide aptamers of the present invention may be comprised of ribonucleotides only (RNA aptamers), deoxyribonucleotides only (DNA aptamers), or a combination of ribonucleotides and deoxyribonucleotides. The nucleotides may be naturally occurring nucleotides (e.g., ATP, TTP, GTP, CTP, UTP) or modified nucleotides. Modified nucleotides refers to nucleotides comprising bases such as, for example, adenine, guanine, cytosine, thymine, and uracil, xanthine, inosine, and queuosine that have been modified by the replacement or addition of one or more atoms or groups. Some examples of types of modifications that can comprise nucleotides that are modified with respect to the base moieties, include but are not limited to, alkylated, halogenated, thiolated, aminated, amidated, or acetylated bases, in various combinations. More specific examples include 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety (e.g., 2'-fluoro or 2'-O-methyl nucleotides), as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. The term nucleotide is also meant to include what are known in the art as universal bases. By way of example, universal bases include but are not limited to 3-nitropyrrole, 5-nitroindole, or nebularine. Modified nucleotides include labeled nucleotides such as radioactively, enzymatically, or chromogenically labeled nucleotides).

The OPN aptamer may by synthesized by any method known to those of skill in the art. In one embodiment, OPN aptamers may be produced by chemical synthesis of oligonucleotides and/or ligation of shorter oligonucleotides.

The chimeric polynucleotides disclosed herein link an OPN aptamer with an OPN-specific therapeutic oligonucleotide. A therapeutic oligonucleotide can include any oligonucleotide that can alter the level of a target molecule. Thus the activity of a therapeutic oligonucleotide includes altering the level of a target molecule. The target molecule of a therapeutic oligonucleotide can be a microRNA, siRNA, any inhibitory RNA, mRNA, DNA, protein, or any other molecule of interest. In certain embodiments, the target molecule participates in a disease state or is a symptom or cause of unhealthy tissue or an unhealthy condition as disclosed elsewhere herein. Accordingly, a therapeutic oligonucleotide can reduce any symptom of unhealthy tissue, such as inflammation. In some embodiments, the target molecule is an inhibitory molecule (e.g., miRNA), such that the therapeutic oligonucleotide binds the inhibitory molecule and removes the repression (e.g., upregulates, increases, or de-represses) of the subject of the target molecule. A therapeutic oligonucleotide can comprise a microRNA, antiMicro RNA oligonucleotide (antimiR), double stranded RNA interference oligonucleotide, double stranded RNA with microRNA activity, antisense oligonucleotide, pre-miRNA, a mRNA coding for microRNAs, or shRNAs, or any oligonucleotide that alters the level of a target molecule. The term "OPN-specific therapeutic oligonucleotide" refers to a therapeutic oligonucleotide specific for a target at or near the site of OPN expression. Thus, an OPN-specific therapeutic oligonucleotide can alter the level of a target molecule in the presence of OPN.

In some embodiments, the OPN-specific therapeutic oligonucleotide comprises a premiRNA or an miRNA that specific for a disease state or unhealthy condition as described herein. For example, the OPN-specific therapeutic oligonucleotide can comprise premiR-30e or an active variant or fragment thereof. In specific embodiments, an OPN aptamer/premiR-30e polynucleotide or active variant or fragment thereof is provided. PremiR-30e can comprise the nucleotide sequence: GCAGUCUUUGCUACUGUAAACAUCCUUGACUGGAAGCUGUAAGGUGUUCA GAGGAGCUUUCAGUCGGAUGUUUACAGCGGCAGGCUGCCA (SEQ ID NO: 2) or an active variant or fragment thereof. In such an embodiment, the OPN Aptamer-miR-30e chimera comprises <u>GCCACAGAAUGAAAAACCUCAUCGAUGUUGCAG</u>CAGUCUUUGCUACUGUA AACAUCCUUGACUGGAAGCUGUAAGGUGUUCAGAGGAGCUUUCAGUCGGA UGUUUACAGCGGCAGGCUGCCA (SEQ ID NO:3), wherein the underlined sequence comprises the OPN aptamer region. Active variant of SEQ ID NO: 3 are also provided.

MiRNAs act as negative regulators of gene expression by inhibiting translation or promoting degradation of target mRNAs. In some embodiments, the OPN-specific therapeutic oligonucleotide comprises an anti-miRNA (antimiR) that can reduce the level of a miRNA that promote a disease state or unhealthy condition. For example, miRNAs that promote a disease state or unhealthy condition include miR-208-5p, which can promote heart disease and cardiac (vascular) remodeling; miR-21-5p which can silence tumor suppressors and promote the progression of heart disease; and miR-20a, which can promote proliferation and invasion of cancer cells and promotes cardiac remodeling. In some embodiments, Thrap1/Med13 is a target of miR-208, Spry1 is a target of miR-21 and Egln3 is a target of miR-20a. Thus, by providing an anti-miRNA that can reduce the level of a miRNA the progression and/or symptoms of a disease state (e.g., heart disease, cardiac remodeling, and/or cancer) can be reduced. Accordingly, the chimeric polynucleotides described herein can comprise an OPN aptamer linked to antimiR-208-5p, an OPN aptamer linked to antimiR-21-5p, and/or an OPN aptamer linked to antimiR-20a. In specific embodiments, antimiR-208-5p can comprise SEQ ID NO: 7 or active fragments or variants thereof; antimiR-21-5p can comprise SEQ ID NO: 8 or active fragments or variants thereof; antimiR-20a can comprise SEQ ID NO: 9 or active fragments or variants thereof.

The OPN aptamer can be directly joined to the OPN-specific therapeutic oligonucleotide or can be joined by a linker or linker polynucleotide. The term "spacer", "spacer polynucleotide", "linker", or "linker polynucleotide" refers to a polynucleotide sequence that acts as a molecular bridge to operably link two different polynucleotides sequences, wherein one portion of the linker is joined to a first polynucleotide sequence, and wherein another portion of the linker is joined to a second polynucleotides sequence. The length of the linker can vary to allow the OPN aptamer to bind OPN while maintaining activity of the OPN-specific therapeutic oligonucleotide. For example, the linker can be several nucleotides in length. Thus, the linker can e.g. comprise between 5 to 3500 nucleotides. In specific embodiments, the linker comprises about 0, 1, 2, 3, 4, 5, 10, 15, 20, 30, 40, 50, 75, 100, 150, 200, 1-200, 5-100, 10-50, or 20-40 nucleotides.

In specific embodiments, the linker is a sticky bridge linker. As used herein, the sticky bridge (stick) linker will allow attachment, in vitro, of transcribed RNAs which have a complementary bridge sequence to the OPN aptamers as described in Zhou J, et al. (*Mol. Ther.* 2013: 21:192-200), for siRNAs. In this manner an OPN aptamer can be joined to an OPN-specific therapeutic oligonucleotide such that the OPN aptamer can bind OPN while maintaining activity of the OPN-specific therapeutic oligonucleotide. In some embodiments a sticky bridge linker can comprise SEQ ID NO: 10 (F stick) and/or SEQ ID NO: 11 (R stick) or active fragments or variants thereof. Accordingly, the chimeric polynucleotides described herein can comprise an OPN aptamer linked to antimiR-208-5p with a sticky bridge linker, an OPN aptamer linked to antimiR-21-5p with a sticky bridge linker, and/or an OPN aptamer linked to antimiR-20a with a sticky bridge linker. In specific embodiments, an OPN aptamer linked to antimiR-208-5p with a sticky bridge linker can comprise SEQ ID NO: 4 or active fragments or variants thereof an OPN aptamer linked to antimiR-21-5p with a sticky bridge linker can comprise SEQ ID NO: 5 or active fragments or variants thereof an OPN aptamer linked to antimiR-20a with a sticky bridge linker can comprise SEQ ID NO: 6 or active fragments or variants thereof.

Active variants of any one of SEQ ID NO: 1-11 can share at least 70%, 75%, 80%, 85%, 90%, 91%, 92%, 93%, 94%, 95%, 96%, 97%, 98%, 99% to the polynucleotide sequence as set forth in SEQ ID NO: 1-11. Active fragments of any one of SEQ ID NO: 1-11 can have at least 15, 20, 30, 40, 50, 60, 70, 80, 90, 100 contiguous nucleotides to that of SEQ ID NO: 1-11 or up to the full length sequence. Methods to assay for the activity of such variants and fragments are disclosed elsewhere herein.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

III. Methods of Delivery

The chimeric polynucleotides disclosed herein can be used to deliver OPN-specific therapeutic oligonucleotides directly to cells of interest in a subject. For example, the chimeric polynucleotides can deliver an OPN-specific therapeutic oligonucleotide to tissues that expresses OPN. Given that expression of OPN often correlates with unhealthy tissue, the OPN-specific therapeutic oligonucleotides disclosed herein can be localized to the site of unhealthy tissue by the OPN aptamer. The term "unhealthy tissue" refers to one unhealthy cell or a plurality of unhealthy cells. Unhealthy tissue can include any inflamed tissue, damaged tissue, tissue with cancer cells, sites of tissue remodeling, or any damaged or diseased tissue. In specific embodiments OPN expression is upregulated at the site of unhealthy tissue compared to normal tissue.

Thus, a subject with unhealthy tissue can have a disease or unhealthy condition that results in the unhealthy tissue as a symptom of the disease or unhealthy condition. For example, the subject with unhealthy tissue can have a disease or unhealthy condition including: cancer; metastasis; hyperproliferative diseases such as psoriasis; autoimmune diseases such as systemic lupus erythematosus, rheumatoid arthritis, multiple sclerosis, and diabetes; inflammation, and inflammatory diseases such as vasculitis, nephritis, arthritis, rheumatoid arthritis, atherosclerosis, osteoarthritis, Crohn's disease, and inflammatory bowel disease; bone diseases such as osteoporosis and osteopetrosis; immune disorders; vascular injuries, aortic abdominal aneurysms, sites of tissue remodeling, chronic inflammatory diseases, restenosis; atherosclerosis, multiple sclerosis, cardiovascular disease, heart failure, and/or Parkinson's disease. By "subject" is intended animals. In specific embodiments, subjects are mammals, e.g., primates or humans. In other embodiments, subjects include domestic animals, such as a feline or canine, or agricultural animals, such as a ruminant, horse, swine, poultry, or sheep. In specific embodiments, the subject undergoing treatment with the pharmaceutical formulations of the invention is a human. In some embodiments, the human undergoing treatment can be a newborn, infant, toddler, preadolescent, adolescent or adult. Subjects as disclosed herein may be suffering from the symptoms of a disease or unhealthy condition or may be at risk for a disease or unhealthy condition.

Accordingly, the chimeric polynucleotides disclosed herein can reduce at least one symptom of a disease or unhealthy condition. By "inhibit", "inhibiting", "reduce", or "reducing" a symptom of a disease or unhealthy condition is intended to mean that at least one symptom of a disease or unhealthy condition is statistically lower than the symptom of a disease or unhealthy condition in an appropriate control. For example, delivery of the OPN-specific therapeutic oligonucleotides can reduce inflammation and tissue remodeling (e.g., cardiac tissue remodeling). In particular embodiments, reduction of at least one symptom of a disease or unhealthy condition according to the presently disclosed methods results in at least about a 95% decrease, at least about a 90% decrease, at least about a 80% decrease, at least about a 70% decrease, at least about a 60% decrease, at least about a 50% decrease, at least about a 40% decrease, at least about a 30% decrease, at least about a 20% decrease, at least about a 10% decrease, or at least about a 5% decrease of the at least one symptom of a disease or unhealthy condition when compared to an appropriate control. In other embodiments, reducing at least one symptom of a disease or unhealthy condition results in a decrease of about 3% to about 15%, about 10% to about 25%, about 20% to about 35%, about 30% to about 45%, about 40% to about 55%, about 50% to about 65%, about 60% to about 75%, about 70% to about 90%, about 70% to about 80%, about 70% to about 85%, about 80% to about 95%, about 90% to about 100% of the at least one symptom when compared to an appropriate control.

The term "administer" or "administering" refers to any method of providing the chimeric polynucleotide disclosed herein to the unhealthy tissue or to a region where the chimeric polynucleotide can be transported to the unhealthy tissue or to the site of OPN expression. In specific embodiments, the chimeric polynucleotides disclosed herein deliver an OPN-specific therapeutic oligonucleotide to unhealthy tissue in vitro. For example, an OPN-specific therapeutic oligonucleotide can be delivered to cells of unhealthy tissue in an in vitro cell culture. In some embodiments, the cells of unhealthy tissue in an in vitro cell culture can include cardiac cells, cardiac smooth muscle cells, cardiac fibroblasts, and/or plaque cells (e.g., thoracic plaque). In some embodiments, OPN-specific therapeutic oligonucleotides (e.g., antimiRs) can be delivered in vitro into cardiac fibroblasts in full-serum media without transfection reagents.

Linking an OPN-specific therapeutic oligonucleotide to an OPN aptamer allows targeting of the OPN-specific therapeutic oligonucleotide to unhealthy tissue expressing OPN, as described elsewhere herein. Further, linking an OPN-specific therapeutic oligonucleotide to an OPN aptamer can result in internalization of the OPN-specific therapeutic oligonucleotide into a cell of the unhealthy tissue. For example, linking an OPN-specific therapeutic oligonucleotide to an OPN aptamer can result in internalization of the OPN-specific therapeutic oligonucleotide into a cardiac cell, cardiac muscle cell, cardiac myocyte, cardiac fibroblast, endothelial cell, and/or thoracic plaque. In specific embodiments, the OPN-specific therapeutic oligonucleotide is internalized into a cell of unhealthy tissue without a transfection reagent. In this manner, an OPN-specific therapeutic oligonucleotide can be targeted to unhealthy tissue and internalized into the cell without a transfection reagent. Internalization of cells can be measured by any method known in the art including, but not limited to, fluorescence imaging and quantitative PCR (qPCR).

The various chimeric polynucleotides disclosed herein (also referred to herein as "active compounds" or "the respective polynucleotides") can be incorporated into pharmaceutical compositions suitable for administration. Such compositions typically comprise the small molecule, nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal. In addition, it may be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In one embodiment, administration can be by direct injection at the site (or former site) of a cancer that is to be treated. In another embodiment, the therapeutically effective amount of the pharmaceutical composition is delivered in a vesicle, such as liposomes (see, e.g., Langer, *Science* 249:1527-33, 1990 and Treat et al., in *Liposomes in the Therapy of Infectious Disease and Cancer*, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, *Science* 249:1527-33, 1990; Sefton, *Crit. Rev. Biomed. Eng.* 14:201-40, 1987; Buchwald et al., *Surgery* 88:507-16, 1980; Saudek et al., *N. Engl. J. Med.* 321:574-79, 1989). In another example, polymeric materials can be used (see, e.g., Levy et al., *Science* 228: 190-92, 1985; During et al., *Ann. Neurol.* 25:351-56, 1989; Howard et al., *J. Neurosurg.* 71:105-12, 1989). Other controlled release systems, such as those discussed by Langer (*Science* 249:1527-33, 1990), can also be used.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. The various polynucleotides disclosed herein find use in treating a variety of conditions including conditions that require delivering therapeutic oligonucleotides into an inflamed tissue, smooth muscle, endothelial cells, cardiac cells and progenitor/stem cells. In one embodiment, the therapeutic polynucleotide disclosed herein finds use in treating or protecting against cardiac dysfunction. In another embodiment, the therapeutic oligonucleotide protects against or treats pressure overload-induced cardiac dysfunction.

The OPN aptamers of the present invention may optionally be administered in conjunction with other compounds (e.g., therapeutic agents, chemotherapeutic agents) or treatments (e.g., surgical intervention, angioplasties, radiotherapies) useful in treating diseases and disorders associated with OPN. The other compounds or treatments may optionally be administered concurrently. As used herein, the word "concurrently" means sufficiently close in time to produce a combined effect (that is, concurrently may be simultaneously, or it may be two or more events occurring within a short time period before or after each other). The other compounds may be administered separately from the aptamers of the present invention, or the two combined together in a single composition.

In the case of inflammation, inflammatory diseases, autoimmune disease and other such cytokine mediated disorders, the therapeutic agent(s) may include, without limitation, a nonsteroidal anti-inflammatory drug (NSAID) (such as diclofenac, diflunisal, ibuprofen, naproxen and the like), a cyclooxygenase-2 inhibitor (such as celecoxib, rofecoxib and the like), a corticosteroid (such as prednisone, methylprednisone and the like) or other immunosuppressive agent (such as methotrexate, leflunomide, cyclophosphamide, azathioprine and the like), a disease-modifying antirheumatic drug (DMARD) (such as injectable gold, penicilliamine, hydroxychloroquine, sulfasalazine and the like), a TNF-alpha inhibitor (such as etanercept, infliximab and the like), other cytokine inhibitor (such as soluble cytokine receptor, anti-cytokine antibody and the like), other immune modulating agent (such as cyclosporin, tacrolimus, rapamycin and the like) and a narcotic agent (such as hydrocodone, morphine, codeine, tramadol and the like).

As noted above, the present invention provides pharmaceutical formulations comprising the aptamers of the invention, in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art. As a general proposition, a dosage from about 0.001 or 0.01 to about 250 or 500 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 1 mg/kg to about 200 mg/kg may be employed for oral administration. Typically, a dosage from about 0.1 mg/kg to 100 mg/kg may be employed for intramuscular injection. The duration of the treatment is usually once per day for a period of two to three weeks or until the condition is essentially controlled. The treatment may be administered more frequently than once per day (e.g., 2, 3, or 4 times per day) or less frequently than once per day (e.g., once every 2, 3, 4, 5, or 6 days or once every 1, 2, 3, or 4 weeks). Lower doses given less frequently can be used prophylactically to prevent or reduce the incidence of recurrence of the disease.

As demonstrated herein, the OPN Aptamer protects against cardiac dysfunction in a mouse model of TAC/pressure overload and the OPN RNA aptamer delivers to some cells (and in some instances the heart) without the need of transfection or direct injection.

A therapeutically effective amount of a therapeutic polynucleotide disclosed herein can be administered to a subject. By "therapeutically effective amount" is intended an amount that is useful in the treatment, prevention or diagnosis of a disease or condition. As used herein, a therapeutically effective amount of a therapeutic polynucleotide disclosed herein is an amount which, when administered to a subject, is sufficient to achieve a desired effect.

"Treatment" is herein defined as the administration of a therapeutic polynucleotide disclosed herein to a subject, where the subject in need thereof, where the purpose is to cure, heal, alleviate, relieve, alter, remedy, ameliorate, improve, or affect the condition or the symptoms of the subject. By "preventing" is intended that a therapeutically effective amount of the therapeutic polynucleotide disclosed herein is administered to a subject at risk for developing a disorder or disease in order to prevent the development of the disorder or disease.

When administration is for the purpose of treatment, administration may be for either a prophylactic or therapeutic purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a therapeutic polynucleotide disclosed herein can include a single treatment or can include a series of treatments. It will also be appreciated that the effective dosage of a therapeutic polynucleotide disclosed herein used for treatment may increase or decrease over the course of a particular treatment. Changes in dosage may result and become apparent from the results of diagnostic assays as described herein.

In light of the description provided above, the following embodiments are further provided:

1. A chimeric polynucleotide comprising an OPN aptamer linked to an OPN-specific therapeutic oligonucleotide.

2. The chimeric polynucleotide of embodiment 1, wherein said OPN aptamer comprises a polynucleotide comprising SEQ ID NO: 1 or an active variant or fragment thereof having at least 80%, 90%, 92%, 95%, 96%, 97%, 98%, or 99% sequence identity to SEQ ID NO: 1.

3. The chimeric polynucleotide of embodiments 1 or 2, wherein said OPN-specific therapeutic oligonucleotide comprises a microRNA, antiMicro RNA oligonucleotide (antimiR), double stranded RNA interference oligonucleotide, double stranded RNA with microRNA activity, antisense oligonucleotide, pre-miRNA, or a mRNA coding for microRNAs, or shRNAs.

4. The chimeric polynucleotide of embodiment 3, wherein the OPN-specific therapeutic oigonuclotide comprises an antimiR specific for an miRNA, wherein the mRNA target of the miRNA is Thrap1, Med13, Spry1, and/or Egln3.

5. The chimeric polynucleotide of embodiment 4, wherein the mRNA target is
   a) Thrap1 or Med13 and the miRNA comprises miR-208-5p;
   b) Spry1 and the miRNA comprises miR-21-5p; or
   c) Egln3 and the miRNA comprises miR-20a.

6. The chimeric polynucleotide of embodiment 5, wherein the miRNA comprises
   a) miR-208-5p and the antimiR comprises the nucleotide sequence set forth in SEQ ID NO: 7 or active fragments or variants thereof having at least 80%, 90%, 92%, 95%, 96%, 97%, 98%, or 99% sequence identity to SEQ ID NO: 7;
   b) miR-21-5p and the antimiR comprises the nucleotide sequence set forth in SEQ ID NO: 8 or active fragments or variants thereof having at least 80%, 90%, 92%, 95%, 96%, 97%, 98%, or 99% sequence identity to SEQ ID NO: 8; or
   c) miR-20a and the antimiR comprises the nucleotide sequence set forth in SEQ ID NO: 9 or active fragments or variants thereof having at least 80%, 90%, 92%, 95%, 96%, 97%, 98%, or 99% sequence identity to SEQ ID NO: 9.

7. The chimeric polynucleotide of embodiment 3, wherein the miRNA comprises miR-30e.

8. The chimeric polynucleotide of embodiment 7, wherein miR-30e comprises the nucleotide sequence set forth in SEQ ID NO: 2 or active fragments or variants thereof having at least 80%, 90%, 92%, 95%, 96%, 97%, 98%, or 99% sequence identity to SEQ ID NO: 2.

9. The chimeric polynucleotide of any one of embodiments 1-3, wherein the chimeric polynucleotide comprises a nucleotide sequence selected from the group consisting of SEQ ID NOs: 3, 4, 5, and 6, or an active variant or fragment thereof having at least 80%, 90%, 92%, 95%, 96%, 97%, 98%, or 99% sequence identity to SEQ ID NO: 3, 4, 5, or 6.

10. The chimeric polynucleotide of any one of embodiments 1-9, wherein the OPN aptamer is directly linked to the OPN-specific therapeutic oligonucleotide.

11. The chimeric polynucleotide of any one of embodiments 1-9, wherein the OPN aptamer comprises a linker.

12. The chimeric polynucleotide of embodiment 11, wherein the linker is a sticky bridge linker.

13. A method of delivering an OPN-specific therapeutic oligonucleotide to unhealthy tissue comprising administering a chimeric polynucleotide comprising an OPN aptamer linked to the OPN-specific therapeutic oligonucleotide.

14. The method of embodiment 13, wherein said OPN aptamer comprises a polynucleotide comprising SEQ ID NO: 1 or an active variant or fragment thereof.

15. The method of embodiment 13 or 14, wherein said OPN-specific therapeutic oligonucleotide comprises a microRNA (miRNA), antiMicro RNA (antimiR), double stranded RNA interference oligonucleotide, double stranded RNA with microRNA activity, antisense oligonucleotide, pre-miRNA, other aptamers, or a mRNA coding for microRNAs, or shRNAs.

16. The method of embodiment 15, wherein the OPN-specific therapeutic oligonucleotide comprises an antimiR, wherein the level of the miRNA corresponding to the antimiR is decreased, and wherein the level of the mRNA target of the miRNA is increased following delivery of the OPN-specific therapeutic oligonucleotide.

17. The method of embodiment 16, wherein the mRNA target is Thrap1/Med13, Spry1, and/or Egln3.

18. The method of embodiment 17, wherein the mRNA target is:
   a) Thrap1 or Med13 and the miRNA comprises miR-208-5p;
   b) Spry1 and the miRNA comprises miR-21-5p; or
   c) Egln3 and the miRNA comprises miR-20a.

19. The method of embodiment 18, wherein the miRNA comprises:
   a) miR-208-5p and the antimiR comprises the nucleotide sequence set forth in SEQ ID NO: 7 or active fragments or variants thereof having at least 80%, 90%, 92%, 95%, 96%, 97%, 98%, or 99% sequence identity to SEQ ID NO: 7;
   b) miR-21-5p and the antimiR comprises the nucleotide sequence set forth in SEQ ID NO: 8 or active fragments or variants thereof having at least 80%, 90%, 92%, 95%, 96%, 97%, 98%, or 99% sequence identity to SEQ ID NO: 8; or
   c) miR-20a and the antimiR comprises the nucleotide sequence set forth in SEQ ID NO: 9 or active fragments or variants thereof having at least 80%, 90%, 92%, 95%, 96%, 97%, 98%, or 99% sequence identity to SEQ ID NO: 9.

20. The method of embodiment 15, wherein the miRNA comprises miR-30e.

21. The method of embodiment 20, wherein miR-30e comprises the nucleotide sequence set forth in SEQ ID NO: 2 or active fragments or variants thereof having at least 80%, 90%, 92%, 95%, 96%, 97%, 98%, or 99% sequence identity to SEQ ID NO: 2.

22. The method of any one of embodiments 13-21, wherein the OPN aptamer is directly linked to the OPN-specific therapeutic oligonucleotide.

23. The method of any one of embodiments 13-21, wherein the OPN aptamer is linked to the OPN-specific therapeutic oligonucleotide with a linker.

24. The method of embodiment 23, wherein the linker is a sticky bridge linker.

25. The method of any one of embodiments 13-15 or 22-25, wherein the chimeric polynucleotide comprises a nucleotide sequence selected from the group consisting of SEQ ID NO: 3, 4, 5, and 6, or an active variant or fragment thereof having at least 80%, 90%, 92%, 95%, 96%, 97%, 98%, or 99% sequence identity to SEQ ID NO: 3, 4, 5, or 6.

26. The method of any one of embodiments 13-25, wherein a therapeutically effective amount of the OPN-specific therapeutic oligonucleotide is delivered to the unhealthy tissue.

27. The method of any one of embodiments 13-26, wherein the OPN-specific therapeutic oligonucleotide is internalized into cells of the unhealthy tissue.

28. The method of any one of embodiments 13-27, wherein the unhealthy tissue expresses OPN.

29. The method of any one of embodiments 13-28, wherein the unhealthy tissue comprises inflamed tissue.

30. The method of embodiment 29, wherein the inflammation is reduced following delivery of the OPN-specific therapeutic oligonucleotide to the unhealthy tissue.

31. The method of any one of embodiments 13-30, wherein the unhealthy tissue is cardiac tissue.

32. The method of embodiment 31, wherein the OPN-specific therapeutic oligonucleotide is internalized by cardiac muscle cells, cardiac fibroblasts, and/or thoracic plaque.

33. The method of any one of embodiments 13-32, wherein the OPN-specific therapeutic oligonucleotide is delivered to cells of unhealthy tissue in vitro.

34. The method of any one of embodiments 13-32, wherein the OPN-specific therapeutic oligonucleotide is delivered to cells of unhealthy tissue in a subject 35. The method of embodiment 34, wherein the subject has an unhealthy condition selected from the group consisting of: inflammation, Crohn's disease, cancer, atherosclerosis, aortic abdominal aneurysms, autoimmune diseases, lupus, multiple sclerosis, rheumatoid arthritis, cardiovascular disease, heart failure, and Parkinson's disease.

36. The method of embodiment 35, wherein at least one symptom of the unhealthy condition is reduced.

37. The method of any one of embodiments 34-36, wherein the subject comprises an OPN receptor and wherein the OPN-specific therapeutic oligonucleotide does not bind said OPN receptor.

38. The method of any one of embodiments 13-37, wherein the chimeric polynucleotide is formulated as a pharmaceutical composition.

39. The method of any one of embodiments 13-38, wherein no transfection reagent is administered for delivery of the OPN-specific therapeutic oligonucleotide.

As used herein, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

The subject matter of the present disclosure is further illustrated by the following non-limiting examples.

EXPERIMENTAL

Example 1

Materials and Reagents

Antibodies against PI3K, CNN1, and TUBULIN were bought from Cell Signaling, Abcam, and Santa Cruz Biotechnology, (Santa Cruz, Calif.) respectively; antibody against OPN and OPN DuoSet Elisa kit were purchased from R&D system. Amersham ECL and Femto Western detection system were obtained from GE Healthcare Bio-Sciences (Piscataway, N.J.). The MirVana PARIS kit used for microRNA, RNA and protein isolations, and the reagents for realtime quantitative PCR were obtained from LifeTechnologies (Carlsbad, Calif.). Durascribe T7 Transcription kits were purchased from Epicentre (Madison, Wis.). LNA miR-30e and scrambled probes for ISH were obtained as double DIG labeled from Exiqon (Woburn, Mass.). 2'OMe OPN aptamer labeled with FAM at the 3' end was ordered from IDT. The Mouse Embryonic Fibroblasts (MEFs) were generously provided by the lab of Dr. Fangliang Zhang at the University of Miami.

MSC Isolation

MSCs were isolated from the femurs and tibias of C57Bl6 3-month old male mice as previously described (Gomes S A et al, PNAS 2013), passaged at least 10 times and then treated or transfected with oligonucleotides.

SMC Isolation

SMCs were isolated from mouse aortic tissue. Briefly, aortas were dissected from 2-3 month old C57Bl6 mice, digested for 15 minutes in Collagenase II, cut into few pieces, and placed on a fibronectin-coated dishes. SMCs grew out of the explants and were passaged after a week.

Transcribing 2'F miR-30e, OPN Aptamer, and OPN-Aptamer-miR-30e Chimera

Templates for the sense and nonsense strands of premiR-30e, OPN aptamer, or OPN-aptamer-miR-30e chimera were generated as Ultramer DNA oligos (IDT), annealed at 95 C for 5 mins, cooled down to room temperature, then transcribed to 2'F RNA oligos using Durascribe T7 enzyme kit following manufacturer's protocol. Final product was DNase I digested and purified on Acrylamide/Urea gel before transfection or treatment into cells.

Western Blots

Cells were lysed using Cell Disruption Buffer (Mirvana Paris Kit) and total cell lysates were subjected to SDS-PAGE and transferred to nitrocellulose. Equal gel transfer was documented by Ponceau Red staining of membranes. Membranes were blocked for 1 h at RT in 5% nonfat milk in TBS-T buffer (Tris 20 mM, NaCl 137 mM, 0.5% Tween-20 pH 7.5), incubated overnight at 4 C with primary antibodies, washed 3× in TBS-T, followed by incubation with horseradish peroxidase-conjugated secondary antibody. After 3 final 10 min TBST washes, proteins were imaged by chemiluminescence, and bands were digitized and analyzed using Image J software (NIH, Bethesda, Md.).

Quantitative RT-PCR

MicroRNA Reverse transcription was performed by specific miR primers LifeTechnologies (Carlsbad, Calif.). cDNA was amplified using TaqMan Universal No UMG PCR master mix reagent and manufacturer's protocol. TaqMan microRNA assays were run in duplicate for each gene in each sample (n=at least 3 biological replicates/condition) and all microRNA levels were normalized to endogenous SNO levels.

In Situ Hybridization

MSCs were fixed with 4% PFA for 15 mins and then hybridized with miR-30e or a SCR double DIG labeled probe using protocol described by Obernosterer et al (Nature Protocols 2007).

ELISA 1 ml media was collected from tissue culture plates and used for OPN ELISA using manufacturer's protocol (R&D).

Thoracic Aortic Constriction (TAC)

C57Bl6 male mouse (~25 g) was subjected to aortic banding. 4 weeks later, one injection of FAM-labeled OPN aptamer was given via tail vein. 24 hours later, the heart was collected for histology.

Example 2

Objective

Osteopontin (OPN) expression increases in the heart during hypertrophy and heart failure. OPN knockout mice subjected to pressure overload by transaortic constriction (TAC) were reported to have a reduced hypertrophic response. We hypothesized that use of an RNA aptamer targeting OPN protein would be an effective, cardiac-specific approach to modulating the hypertrophic response to overload stress.

Method and Results:

C57BL6 male mice were subjected to sham or TAC surgeries. TAC mice were injected with 2'OMe OPN RNA aptamer, 2' OMe mutant OPN aptamer, or PBS. Each treated mouse received a total of 10 injections—one jugular injection during surgery, followed by 9 tail vein injections every other day. Cardiac function was measured by echocardiography at 4 and 6 wks post TAC. At 4 wks, the OPN aptamer group (n=13) showed increase in % EF (25%) and % FS (35%), and decrease in LVPWd (0.63 fold)—p<0.01 for all, relative to mut group (n=13). Identical significant improvement was recorded relative to the PBS group (n=3) with no significant difference to the normal Sham and no-surgery group (n=11). This significant cardiac improvement was sustained at 6 wks post surgery. At 4 wks post TAC, qPCR, western blots, and histology were performed on left ventricular (LV) samples. OPN aptamer treatment reduced (p<0.05) the expression of Nppb, Opn, and Col3a1 transcripts relative to mut aptamer group (n=5/group). OPN and downstream targets FN1, PI3K, and p-AKT proteins were reduced (p<0.05) in the OPN aptamer-treated LVs relative to mut group (n=4-6/group). Picrosirius Red and Wheat Germ Agglutinin staining showed respectively that the OPN aptamer reduced cardiac fibrosis (0.32 fold) and myocyte cross sectional area (0.77 fold)—p<0.01. In neonatal rat cardiac myocytes, 24 h treatment with 250 nM FAM-labeled OPN aptamer, followed by Actinin immunostaining and microscopy, showed impressive intracellular uptake of the OPN aptamer by the cardiac myocytes.

Conclusion:

OPN RNA aptamer protected against cardiac dysfunction in the mouse TAC model of cardiac hypertrophy. The cardioprotective effect of the OPN aptamer, together with the efficient uptake by cardiomyocytes make it a therapeutic molecule and a platform for targeted RNA delivery into the heart.

Example 3

C57BL6 male mice were subjected to sham or TAC surgeries. TAC mice were injected with 17 ug of OPN aptamer (Apt), 17 ug of mutant OPN aptamer (M-Apt), or PBS. Each treated mouse received a total of 10 injections—a left subclavian vein injection during surgery, followed by 9 tail vein injections every other day. Cardiac function was measured by echocardiography at 4, 8 and 12 wks post TAC. At 4 wks, the OPN aptamer group (n=13) showed increase in % EF (25%) and % FS (35%), and decrease in LVPWd (0.63 fold)—p<0.01 for all, relative to mut group (n=13/group). Identical significant improvement was recorded relative to the PBS group (n=3) with no significant difference to the normal Sham and no-surgery group (n=11). This significant cardiac improvement was sustained at 8 wks (n=7/group) and 12 wks (n=4-7/group) post surgery. To assess effect of OPN aptamer on reversal of cardiac remodeling, at 8 wks post TAC (n=5-6), cardiac function was assessed followed by a total of 11 OPN aptamer injections (one every other day), and then assessed again at 10 wks. The OPN aptamer improved % EF in TAC mice (0.6 fold p=0.02 TAC vs Sham before treatment to 0.85 fold p=NS after treatment). To track OPN aptamer deliver into the heart, 3 month TAC mouse was injected with 1 nmol (~15 ug) of DIG-labeled OPN aptamer. After 10 hours, mouse was sacrificed, and heart processed for staining and microscopy.

As demonstrated in FIG. 8, single tail vein injection of labeled OPN aptamer in 3 month TAC (Trans-Aortic Constriction) mouse shows strong uptake by cardiac cells, as demonstrated by blue/purple precipitation in panel (A) or green immunofluorescence in panel (B). Note that the 2 staining methods yield the same results showing main oligonucleotide uptake by outer myocardial wall. Arrows=cardiac myocytes; Arrowheads=cardiac fibroblasts; Dotted arrow=Endothelial cells.

The full scan of the heart section and the high magnification images show in an unbiased manner the real distribution of the injected therapeutic oligonucleotides.

Compared to the published literature on oligonucleotide delivery to the heart, our results show superior/specific delivery to the remodeling areas of the heart (from a single tail vein injection).

Example 4

Mouse neonatal cardiac fibroblasts were treated with different concentration of OPN-aptamer-antimiR conjugates in cardiac media (containing 15% serum). After 43 hours, cells were collected and assayed for microRNA and gene target expression by qPCR.

As reported in FIGS. 9-11, mouse neonatal cardiac fibroblasts were treated (without any transfection reagents) with one of three OPN-aptamer-antimiR conjugates for 43 hours. (A) Secondary structure of the conjugates was determined by RNAstructure software. (B) qPCR shows knockdown of corresponding microRNAs, and de-preperession of their mRNA targets.

1st successful delivery of antimiRs into cardiac fibroblasts in full-serum media without transfection reagents.

Knock down of non-targeted miRs is less with lower dosages of the conjugates.

Example 5

To track OPN aptamer deliver into atherogeninc plaque, 8 month old ApoE−/− mouse, fed a high fat diet for 2 months, was injected with 2 nmol (~30 ug) of DIG-labeled OPN aptamer. After 10 hours, mouse was sacrificed, and aortic plaque processed for staining and microscopy.

As reported in FIG. 12, a single tail vein injection of labeled OPN aptamer (green) in 8 month atherogenic ApoE−/− mouse shows successful uptake by the thoracic plaque, as shown by immunofluorescence and confocal microscopy.

We believe that the biggest advantage for using the OPN aptamer for delivering of oligonucleotides is the specific homing to the diseased tissue (mediated by paracrine OPN/OPN receptor expression).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of delivering a therapeutic oligonucleotide into cells of unhealthy tissue comprising administering a chimeric polynucleotide comprising an osteopontin (OPN) aptamer linked to the therapeutic oligonucleotide, wherein the therapeutic oligonucleotide is not another OPN aptamer, wherein delivery is mediated by binding of the chimeric polynucleotide to OPN and binding of OPN to OPN receptor on the surface of the cells, allowing uptake of the chimeric polynucleotide into the cells of the unhealthy tissue, wherein the therapeutic oligonucleotide exerts a therapeutic effect inside the cells, and wherein no transfection reagent, liposomes, or cationic polymers are administered for delivery of the therapeutic oligonucleotide, and wherein the unhealthy tissue is cardiac tissue, atherogenic plaque, 4T1 breast cancer cells, smooth muscle cells, mesenchymal stem cells, cardiac fibroblasts, limbal stem cells, retinal pigment epithelial cells, or mouse embryonic fibroblasts.

2. The method of claim 1, wherein said OPN aptamer comprises a polynucleotide comprising SEQ ID NO: 1 or an active variant or fragment thereof.

3. The method of claim 1, wherein a therapeutically effective amount of the therapeutic oligonucleotide is delivered to the unhealthy tissue.

4. The method of claim 1, wherein the unhealthy tissue expresses OPN.

5. The method of claim 1, wherein the therapeutic oligonucleotide is delivered to cardiac tissue, atherogenic plaque, smooth muscle cells, or cardiac fibroblasts.

6. The method of claim 1, wherein the chimeric polynucleotide is formulated as a pharmaceutical composition.

7. The method of claim 1, wherein said therapeutic oligonucleotide comprises a microRNA (miRNA), an anti-Micro RNA (antimiR), a double stranded RNA interference oligonucleotide, a double stranded RNA with microRNA activity, an antisense oligonucleotide, a pre-miRNA, an aptamer, a mRNA coding for a microRNA, or an mRNA coding for an shRNA.

8. The method of claim 7, wherein the therapeutic oligonucleotide comprises an antimiR, wherein the level of the miRNA corresponding to the antimiR is decreased, and wherein the level of the mRNA target of the miRNA is increased following delivery of the therapeutic oligonucleotide.

9. The method of claim 1, wherein the OPN aptamer is directly linked to the therapeutic oligonucleotide.

10. The method of claim 1, wherein the OPN aptamer is linked to the therapeutic oligonucleotide with a linker.

11. The method of claim 10, wherein the linker is a sticky bridge linker.

12. The method of claim 1 wherein the unhealthy tissue comprises inflamed tissue.

13. The method of claim 12, wherein the inflammation is reduced following delivery of the therapeutic oligonucleotide to the unhealthy tissue.

14. The method of claim 5, wherein the cardiac tissue comprises cardiac muscle cells, cardiac fibroblasts, or thoracic plaque.

15. The method of claim 1, wherein the therapeutic oligonucleotide is delivered to cells of unhealthy tissue in vitro, or to stem cells.

16. The method of claim 1, wherein the therapeutic oligonucleotide is delivered to cells of unhealthy tissue in a subject.

17. The method of claim 16, wherein the subject has an unhealthy condition selected from the group consisting of: inflammation, Crohn's disease, cancer, atherosclerosis, aortic abdominal aneurysms, autoimmune diseases, lupus, multiple sclerosis, rheumatoid arthritis, cardiovascular disease, heart failure, and Parkinson's disease.

18. The method of claim 17, wherein at least one symptom of the unhealthy condition is reduced.

19. The method of claim 16 wherein the subject comprises an OPN receptor and wherein the therapeutic oligonucleotide does not bind said OPN receptor.

20. The method of claim 1, wherein said OPN aptamer comprises ribonucleotides only, deoxyribonucleotides only, or a combination of ribonucleotides and deoxyribonucleotides.

21. The method of claim 20, wherein said OPN aptamer is an RNA OPN aptamer.

22. The method of claim 20, wherein the therapeutic oligonucleotide comprises a DNA sequence or an RNA aptamer.

* * * * *

SEQUENCE LISTING

<160> NUMBER OF SEQ ID NOS: 12

<210> SEQ ID NO 1
<211> LENGTH: 32
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(32)
<223> OTHER INFORMATION: OPN aptamer

<400> SEQUENCE: 1
gccacagaau gaaaaaccuc aucgauguug ca                           32

<210> SEQ ID NO 2
<211> LENGTH: 90
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(90)
<223> OTHER INFORMATION: PremiR-30e

<400> SEQUENCE: 2
gcagucuuug cuacuguaaa cauccuugac uggaagcugu aagguguuca gaggagcuuu    60
cagucggaug uuuacagcgg caggcugcca                                    90

<210> SEQ ID NO 3
<211> LENGTH: 122
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(35)
<223> OTHER INFORMATION: OPN aptamer
<220> FEATURE:
<221> NAME/KEY: misc_feature
<222> LOCATION: (36)...(122)
<223> OTHER INFORMATION: PremiR-30e
<220> FEATURE:
<221> NAME/KEY: misc_feature
<222> LOCATION: (1)...(122)
<223> OTHER INFORMATION: OPN Aptamer-miR-30e chimera

<400> SEQUENCE: 3
gccacagaau gaaaaaccuc aucgauguug cagcagucuu ugcuacugua aacauccuug    60
acuggaagcu guaaggyguuu cagaggagcu uucagucgga uguuuacagc ggcaggcugc   120
ca                                                                  122

<210> SEQ ID NO 4
<211> LENGTH: 85
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(32)
<223> OTHER INFORMATION: OPN aptamer
<220> FEATURE:
<221> NAME/KEY: misc_feature
<222> LOCATION: (33)...(66)
<223> OTHER INFORMATION: sticky bridge

```
<220> FEATURE:
<221> NAME/KEY: misc_feature
<222> LOCATION: (66)...(85)
<223> OTHER INFORMATION: antimiR-208-5p
<220> FEATURE:
<221> NAME/KEY: misc_feature
<222> LOCATION: (1)...(85)
<223> OTHER INFORMATION: OPN aptamer linked to antimiR-208-5p with a
      sticky bridge linker

<400> SEQUENCE: 4
gccacagaau gaaaaaccuc aucgauguug caggcuaucu agaauguacg uacauucuag    60
auagccauaa cccgggccaa aagct                                         85

<210> SEQ ID NO 5
<211> LENGTH: 84
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(32)
<223> OTHER INFORMATION: OPN Aptamer
<220> FEATURE:
<221> NAME/KEY: misc_feature
<222> LOCATION: (33)...(66)
<223> OTHER INFORMATION: sticky bridge linker
<220> FEATURE:
<221> NAME/KEY: misc_feature
<222> LOCATION: (67)...(84)
<223> OTHER INFORMATION: antimiR-21-5p
<220> FEATURE:
<221> NAME/KEY: misc_feature
<222> LOCATION: (1)...(84)
<223> OTHER INFORMATION: OPN aptamer linked to antimiR-21-5p with a
      sticky bridge linker

<400> SEQUENCE: 5
gccacagaau gaaaaaccuc aucgauguug caggcuaucu agaauguacg uacauucuag    60
auagccacat cagtctgata agct                                          84

<210> SEQ ID NO 6
<211> LENGTH: 87
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(32)
<223> OTHER INFORMATION: OPN Aptamer
<220> FEATURE:
<221> NAME/KEY: misc_feature
<222> LOCATION: (33)...(66)
<223> OTHER INFORMATION: sticky bridge linker
<220> FEATURE:
<221> NAME/KEY: misc_feature
<222> LOCATION: (67)...(87)
<223> OTHER INFORMATION: antimiR-20a
<220> FEATURE:
<221> NAME/KEY: misc_feature
<222> LOCATION: (1)...(87)
<223> OTHER INFORMATION: OPN aptamer linked to antimiR-20a with a sticky
      bridge linker

<400> SEQUENCE: 6
gccacagaau gaaaaaccuc aucgauguug caggcuaucu agaauguacg uacauucuag    60
auagccacct gcactataag cacttta                                       87
```

```
<210> SEQ ID NO 7
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(19)
<223> OTHER INFORMATION: AntimiR-208a-5p

<400> SEQUENCE: 7
ataacccggg ccaaaagct                                                19

<210> SEQ ID NO 8
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(18)
<223> OTHER INFORMATION: AntimiR-21-5p

<400> SEQUENCE: 8
acatcagtct gataagct                                                 18

<210> SEQ ID NO 9
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(21)
<223> OTHER INFORMATION: AntimiR-20a

<400> SEQUENCE: 9
acctgcacta taagcactttt a                                            21

<210> SEQ ID NO 10
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(17)
<223> OTHER INFORMATION: Sticky bridge linker (F stick)

<400> SEQUENCE: 10
ggcuaucuag aauguac                                                  17

<210> SEQ ID NO 11
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(17)
<223> OTHER INFORMATION: Sticky bridge linker (R stick)

<400> SEQUENCE: 11
guacauucua gauagcc                                                  17
```

```
<210> SEQ ID NO 12
<211> LENGTH: 126
<212> TYPE: DNA
<213> ORGANISM: Artificial sequence
<220> FEATURE:
<223> OTHER INFORMATION: Synthetic

<400> SEQUENCE: 12
gggccacaga atgaaaaacc tcatcgatgt tgcagggcag tctttgctac tgtaaacatc      60
cttgactgga agctgtaagg tgttcagagg agctttcagt cggatgttta cagcggcagg     120
ctgcca                                                                126
```